United States Patent [19]

Woitun et al.

[11] Patent Number: 5,726,205

[45] Date of Patent: Mar. 10, 1998

[54] O-ACYL-4-PHENYL-CYCLOHEXANOLS, THEIR SALTS, MEDICAMENTS CONTAINING SUCH COMPOUNDS AND THEIR USE, AS WELL AS A METHOD OF PREPARING THEM

[75] Inventors: Eberhard Woitun; Roland Maier, both of Biberach; Peter Müller, Mittelbiberach; Rudolf Hurnaus, Biberach; Michael Mark, Biberach; Bernard Eisele, Biberach; Ralph-Michael Budzinski, Biberach; Gerhard Hallermayer, Maselheim-Sulmingen, all of Germany

[73] Assignee: Karl Thomae GmbH, Biberach An Der Riss, Germany

[21] Appl. No.: 718,364

[22] PCT Filed: Apr. 25, 1994

[86] PCT No.: PCT/EP94/01276

§ 371 Date: Jan. 17, 1997

§ 102(e) Date: Jan. 17, 1997

[87] PCT Pub. No.: WO95/29148

PCT Pub. Date: Nov. 2, 1995

[51] Int. Cl.⁶ ................................................. A61K 31/135
[52] U.S. Cl. ........................... 514/538; 514/530; 514/531; 560/20; 560/43; 560/61; 560/100
[58] Field of Search .............................. 514/530, 531, 514/540, 538; 560/20, 43, 61, 100

[56] References Cited

U.S. PATENT DOCUMENTS 5,391,571 2/1995 Mewshaw ............................ 514/490
5,455,273 10/1995 Maier ................................... 514/617

FOREIGN PATENT DOCUMENTS 3216281 11/1982 Germany.

OTHER PUBLICATIONS

CA 103: 204217—Abstract of JP60097925 May 31, 1985 "Substituted phenyl cyclohexane derivative as liquid cryst".

*Primary Examiner*—C. Warren Ivy
*Assistant Examiner*—Jean F. Vollano
*Attorney, Agent, or Firm*—Robert P. Raymond; Alan R. Stempel; Mary-Ellen Devlin

[57] ABSTRACT

This document describes O-acyl-4-phenyl-cycloalkanols of general formula I

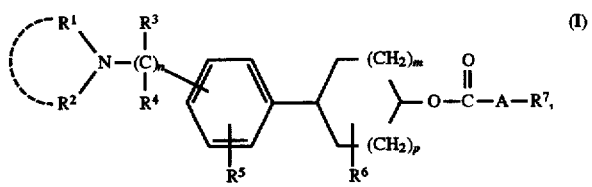

wherein n denotes the number 0 or 1, m denotes the number 1 or 2, p denotes the number 0 or 1, $R^1$ and $R^2$ each denote hydrogen, lower alkyl, alkenyl or alkynyl, which may optionally also be substituted, or together with the nitrogen atom between them denote 5- to 7-membered saturated, monocyclic, heterocyclic rings which may optionally also be interrupted by an oxygen or sulphur atom or by an imino group, $R^3$, $R^4$, $R^5$ and $R^6$ denote hydrogen or lower alkyl, $R^5$ additionally denotes lower alkoxy, $R^7$ denotes hydrogen, cycloalkyl, phenyl or substituted phenyl, naphthyl, tetrahydronaphthyl, thienyl, furyl or pyridyl and A denotes a chemical bond or alkyl, alkenyl or alkynyl having up to 17 carbon atoms, and also processes for preparing them, pharmaceutical compositions containing these compounds and the use of these pharmaceutical compositions which intervene in cholesterol biosynthesis.

The antihypercholesterolaemic substances can be used for the treatment and prophylaxis of atherosclerosis; they inhibit the enzyme 2,3-epoxysqualene-lanosterol-cyclase.

7 Claims, No Drawings

O-ACYL-4-PHENYL-CYCLOHEXANOLS, THEIR SALTS, MEDICAMENTS CONTAINING SUCH COMPOUNDS AND THEIR USE, AS WELL AS A METHOD OF PREPARING THEM

This is the National Phase Application of PCT EP94/01276 field Apr. 25, 1994 now WO95/29148 published Nov. 2, 1995.

The present invention relates to O-acyl-4-phenyl-cycloalkanols, the salts thereof with physiologically acceptable organic and inorganic acids, processes for preparing these compounds and pharmaceutical compositions containing them and the use thereof.

The compounds according to the invention are inhibitors of cholesterol biosynthesis, more particularly inhibitors of the enzyme 2,3-epoxysqualene-lanosterol-cyclase, a key enzyme in cholesterol biosynthesis. The compounds according to the invention are suitable for the treatment and prophylaxis of hyperlipidaemia, hypercholesterolaemia and atherosclerosis. Other possible fields of application consist of the treatment of hyperproliferative skin and vascular disorders, tumours, gallstone problems and mycoses.

Compounds which intervene in cholesterol biosynthesis are of importance in the treatment of a number of syndromes. Particular examples are hypercholesterolaemias and hyperlipidaemias which are risk factors for the development of atherosclerotic vascular changes and their sequelae such as, for example, coronary heart disease, cerebral ischaemia, claudicatio intermittens and gangrene.

The significance of elevated serum cholesterol levels as a main risk factor in the occurrence of atherosclerotic vascular changes is generally recognised. Extensive clinical trials have led to the finding that the risk of coronary heart disease can be reduced by lowering serum cholesterol (Current Opinion in Lipidology 2(4), 234 [1991]). Since the majority of cholesterol is synthesised in the body and only a small proportion is taken in with food, the inhibition of biosynthesis constitutes a particularly attractive method of lowering elevated cholesterol levels.

Other possible fields of application for cholesterol biosynthesis inhibitors consist of the treatment of hyperproliferative skin and vascular disorders as well as tumoral diseases, the treatment and prophylaxis of gallstone problems and use in mycoses. This latter case involves intervention in the ergosterol biosynthesis in fungal organisms, which proceeds to a considerable extent in the same way as cholesterol biosynthesis in mammalian cells.

Cholesterol or ergosterol biosynthesis proceeds, starting from acetic acid, via a large number of reaction steps. This multi-step process presents a series of possible interventions, of which the following may be mentioned by way of example:

For inhibiting the enzyme 3-hydroxy-3-methylglutaryl-coenzyme A (HMG-CoA) synthase, β-lactones and β-lactams with a potential antihypercholesterolaemic activity may be mentioned (see J. Antibiotics 40, 1356 [1987], U.S. Pat. No. 4,751,237, EP-A-0 462 667, U.S. Pat. No. 4,983,597).

Inhibitors of the enzyme HMG-CoA-reductase are 3,5-dihydroxycarboxylic acids of the statin type and the δ-lactones, of which lovastatin, simvastatin and pravastatin are used in the treatment of hypercholesterolaemia.

Other possible uses for these compounds are fungal infections (U.S. Pat. No. 4,375,475, EP-A-0 113 881, U.S. Pat. No. 5,106,992), skin diseases (EP-A-0 369 263) and gallstone problems and tumoral diseases (U.S. Pat. No. 5,106,992; Lancet 339, 1154–1156 [1992]). Another possible therapy is the inhibition of the proliferation of smooth muscle cells using lovastatin (Cardiovasc. Drugs. Ther. 5, Suppl. 3, 354 [1991]).

Inhibitors of the enzyme squalene-synthetase include, for example, isoprenoid-(phosphinylmethyl)phosphonates which have been described as suitable for the treatment of hypercholesterolaemia, gallstone problems and tumoral diseases in EP-A-0 409 181 and in J. Med. Chemistry 34, 1912 [1991], as well as the squalestatins with a cholesterol-lowering and antimycotic effect (J. Antibiotics 45, 639–647 [1992] and J. Biol. Chemistry 267, 11705–11708 [1992].

Known inhibitors of the enzyme squalene-epoxidase are allylamines such as naftifin and terbinafin, which have been used in therapy as drugs to combat fungal diseases, as well as the allylamine NB-598 which has an antihypercholesterolaemic effect (J. Biol. Chemistry 265, 18075–18078, [1990]) and fluorosqualene derivatives having a hypocholesterolaemic effect (U.S. Pat. No. 5,011,859). In addition, piperidines and azadecalins having a potential hypocholesterolaemic and/or antifungal activity have been described, the mechanism of activity of which has not been adequately explained and which constitute squalene epoxidase and/or 2,3-epoxysqualene-lanosterol-cyclase inhibitors (EP-A-0 420 116, EP-A-0 468 434, U.S. Pat. No. 5,084,461 and EP-A-0 468 457).

Examples of inhibitors of the enzyme 2,3-epoxysqualene-lanosterol-cyclase include diphenyl derivatives (EP-A-0 464 465), aminoalkoxybenzyl derivatives (EP-A-0 410 359) and piperidine derivatives (J. Org. Chem. 57, 2794–2803, [1992]) which have an antifungal activity. Moreover, this enzyme is inhibited in mammalian cells by decalins, azadecalins and indane derivatives (WO 89/08450, J. Biol. Chemistry 254, 11258–11263 [1981], Biochem. Pharmacology 37, 1955–1964 [1988] and J 64 003 144) and also by 2-aza-2,3-dihydrosqualene and 2,3-epiminosqualene (Biochem. Pharmacology 34, 2765–2777 [1985]), by squalene-oxide-epoxide-enol ethers (J. Chem. Soc. Perkin Trans. I, 1988, 461) and 29-methylidene-2,3-oxidosqualene (J. Amer. Chem. Soc. 113, 9673–9674 [1991]).

Finally, steroid derivatives having a potential antihyperlipaemic activity may also be mentioned as inhibitors of the enzyme lanosterol-14α-demethylase and at the same time they have an effect on the enzyme HMG-CoA-reductase (U.S. Pat. No. 5,041,432, J. Biol. Chemistry 266, 20070–20078 [1991], U.S. Pat. No. 5,034,548). Furthermore, this enzyme is inhibited by antimycotics of the azole type which constitute N-substituted imidazoles and triazoles. This category includes, for example, the antimycotics ketoconazole and fluconazole which are on the market.

The compounds of general formula I which follows are new. It has been found, surprisingly, that they are highly effective inhibitors of the enzyme 2,3-epoxysqualene-lanosterol-cyclase (International Classification: EC5.4.99.7).

The enzyme 2,3-epoxysqualene-lanosterol-cyclase catalyses a key stage of cholesterol or ergosterol biosynthesis, namely the conversion of 2,3-epoxysqualene into lanosterol, the first compound with a steroid structure in the biosynthesis cascade. Inhibitors of this enzyme lead one to expect the advantage of higher selectivity over inhibitors of earlier biosynthesis stages, such as, for example, HMG-CoA-synthesis and HMG-CoA-reduction, since the inhibition of these early biosynthesis stages leads to a reduction in biosynthetically formed mevalonic acid and, as a result, may have a negative effect on the biosynthesis of the mevalonic acid-dependent substances dolichol, ubiquinone and isopentenyl-t-RNA (cf. J. Biol. Chemistry 265, 18075–18078 [1990]).

In the inhibition of biosynthesis stages after the conversion of 2,3-epoxysqualene into lanosterol there is the risk of the accumulation of intermediate products having a steroidal structure in the body and the triggering of toxic effects connected therewith. This has been described, for example, for triparanol, a desmosterol reductase inhibitor. This substance has had to be taken off the market owing to the formation of cataracts, ichthyosis and alopecia (mentioned in J. Biol. Chemistry 265, 18075–18078 [1990]).

As has already been explained, inhibitors of 2,3-epoxysqualene-lanosterol-cyclase have been individually described in the literature. However, the structures of these compounds are completely different from the structure of the compounds according to the invention which conform to general formula I hereinafter.

The invention relates to the preparation of antihypercholesterolaemic substances suitable for the treatment and prophylaxis of atherosclerosis and, compared with known active substances, characterised by an improved antihypercholesterolaemic activity with greater selectivity and hence increased safety. Since the compounds according to the invention are also able to inhibit ergosterol biosynthesis in fungal organisms, thanks to their considerable effectiveness as inhibitors of the enzyme 2,3-epoxysqualene-lanosterol-cyclase, they are also suitable for the treatment of mycoses.

The present invention relates to new O-acyl-4-phenyl-cycloalkanols of general formula I

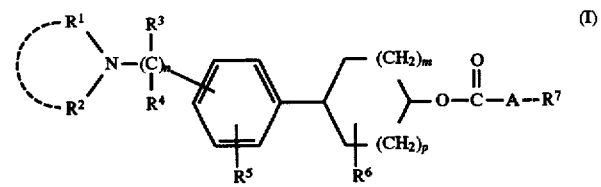

wherein n denotes the number 0 or 1, m denotes the number 1 or 2, p denotes the number 0 or 1, $R^1$ and $R^2$, which may be identical or different, denote a hydrogen atom, a straight-chained or branched $C_{1-6}$-alkyl group, a straight-chained or branched $C_{3-6}$-alkenyl or alkynyl group, the double and triple bonds thereof being isolated from the nitrogen-carbon bond, whilst the above-mentioned alkyl, alkenyl and alkynyl groups may also be substituted by an amino, hydroxy, alkoxy, alkylcarbonyloxy, alkylcarbonylamino, carboxyl, alkoxycarbonyl, aminocarbonyl or cyano group, and the above-mentioned amino, hydroxy, alkoxy, alkylcarbonyloxy and alkylcarbonylamino group may not be bound to an unsaturated carbon atom and may not be bound to the carbon atom in position 1, or $R^1$ and $R^2$ together with the nitrogen atom between them denote a 5- to 7-membered saturated monocyclic heterocyclic ring, whilst in a 6-membered saturated monocyclic heterocyclic ring thus formed a methylene group in the 4-position may be replaced by an oxygen or sulphur atom or by an optionally alkyl-substituted imino group, $R^3$ and $R^4$, which may be identical or different, denote a hydrogen atom or a straight-chained or branched $C_{1-4}$-alkyl group, $R^5$ denotes a hydrogen atom, a straight-chained or branched $C_{1-4}$-alkyl group or a $C_{1-4}$-alkoxy group, $R^6$ denotes a hydrogen atom or a straight-chained or branched $C_{1-4}$-alkyl group, $R^7$ denotes a hydrogen atom, a $C_{3-7}$-cycloalkyl group, a phenyl group optionally mono- or disubstituted by a fluorine, chlorine or bromine atom or by a hydroxy, alkyl, alkoxy, phenylalkoxy, phenyl, nitro, amino, alkylamino, dialkylamino, alkylcarbonylamino, cyano, carboxy, alkoxycarbonyl, aminocarbonyl, alkylaminocarbonyl, dialkylaminocarbonyl, trifluoromethyl, alkylcarbonyloxy, aminosulphonyl, alkylaminosulphonyl or dialkylaminosulphonyl group, wherein the substituents may be identical or different and two adjacent hydrogen atoms in a phenyl group may be replaced by a methylenedioxy or 1,2-ethylenedioxy group, a phenyl group substituted by two chlorine or bromine atoms and an amino group, a naphthyl or tetrahydronaphthyl group, a thienyl, furyl or pyridyl group substituted by a halogen atom or by one or two alkyl groups, and A denotes a bond, a straight-chained or branched $C_{1-17}$-alkylene group or a $C_{2-17}$-alkenylene or alkynylene group, whilst all the above-mentioned alkyl and alkoxy moieties, unless otherwise specified, may contain 1 to 3 carbon atoms, and any halogen atom mentioned hereinbefore may be a fluorine, chlorine or bromine atom, the enantiomers, diastereomers and geometric isomers thereof and the salts thereof, more especially for pharmaceutical use the physiologically acceptable salts with organic or inorganic acids.

The preferred compounds are those of general formula Ia

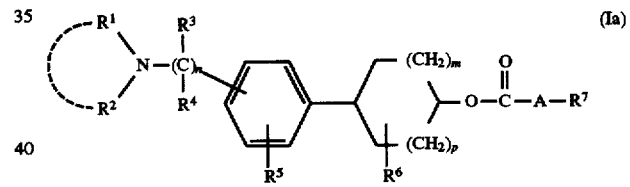

wherein n, m and p each denote the number 1, $R^1$ and $R^2$, which may be identical or different, denote a hydrogen atom, a straight-chained or branched $C_{1-6}$-alkyl group, a straight-chained or branched $C_{3-6}$-alkenyl or alkynyl group, the double and triple bonds thereof being isolated from the nitrogen-carbon bond, whilst the above-mentioned alkyl, alkenyl and alkynyl groups may be substituted by an amino, hydroxy, alkoxy, alkylcarbonyloxy, alkylcarbonylamino, carboxyl, alkoxycarbonyl, aminocarbonyl or cyano group, and the above-mentioned amino, hydroxy, alkoxy, alkylcarbonyloxy and alkylcarbonylamino group may not be bound to an unsaturated carbon atom and may not be bound to the carbon atom in position 1, or $R^1$ and $R^2$ together with the nitrogen atom between them denote a 5- to 7-membered saturated monocyclic heterocyclic ring, whilst in a 6-membered saturated monocyclic heterocyclic ring thus formed a methylene group in the 4-position may be replaced by an oxygen or sulphur atom or by an optionally alkyl-substituted imino group, $R^3$ to $R^6$, which may be identical or different, each denote a hydrogen atom or a methyl group, $R^7$ denotes a hydrogen atom, a $C_{3-7}$-cycloalkyl group, a phenyl group optionally mono- or disubstituted by a fluorine, chlorine or bromine atom or by a hydroxy, alkyl, alkoxy, phenylalkoxy, phenyl, nitro, amino, alkylamino, dialkylamino, alkylcarbonylamino, cyano, carboxy, alkoxycarbonyl, aminocarbonyl, alkylaminocarbonyl, dialkylaminocarbonyl, trifluoromethyl, alkylcarbonyloxy, aminosulphonyl, alkylaminosulphonyl or dialkylaminosulphonyl group, whilst the substituents may be identical or different and two adjacent hydrogen atoms in a phenyl group may be replaced by a methylenedioxy or 1,2-ethylenedioxy group, a phenyl group substituted by two chlorine or bromine atoms and an amino group, a naphthyl or tetrahydronaphthyl group, a thienyl, furyl or pyridyl group substituted by a chlorine or bromine atom or by one or two alkyl groups, and A denotes a bond, a straight-chained or branched $C_{1-10}$-alkylene group or a $C_{2-10}$-alkenylene or alkynylene group, wherein all the above-mentioned alkyl and alkoxy moieties, unless otherwise specified, may contain 1 to 3 carbon atoms, the enantiomers, diastereomers and geometric isomers thereof and the salts thereof, particularly for pharmaceutical use the physiologically acceptable salts thereof with inorganic or organic acids.

Particularly preferred compounds are those of general formula Ia wherein n, m and p each denote the number 1, $R^1$ denotes a hydrogen atom, a straight-chained or branched $C_{1-4}$-alkyl group which may be substituted by an aminocarbonyl group or, in the 2-, 3- or 4-position by a hydroxy or alkoxy group, or a 2-propenylene group, and $R^2$ denotes a hydrogen atom, a $C_{1-4}$-alkyl group or a 2-propenylene group, or $R^1$ and $R^2$ together with the nitrogen atom between them denote a 5- or 6-membered saturated monocyclic heterocyclic ring, whilst in a 6-membered saturated monocyclic heterocyclic ring thus formed, a methylene group in the 4-position may be replaced by an oxygen atom or by an optionally alkyl-substituted imino group, $R^3$ to $R^6$ each denote a hydrogen atom, $R^7$ denotes a hydrogen atom, a $C_{3-6}$-cycloalkyl group, a phenyl group optionally monosubstituted in the 4-position by a fluorine, chlorine or bromine atom or by an alkyl, alkoxy, phenyl, nitro or trifluoromethyl group, a phenyl group disubstituted by two chlorine atoms, one chlorine atom and an alkyl or amino group or two alkoxy groups, a phenyl group trisubstituted by two chlorine atoms and an amino group, a 3,4-methylenedioxyphenyl group, a naphthyl or tetrahydronaphthyl group, a 2-furyl group or a 2-thienyl group optionally substituted by a chlorine atom in the 5-position or a 3-pyridyl group, A denotes a bond, a straight-chained or branched $C_{1-6}$-alkylene group or a $C_{2-5}$-alkenylene group, whilst all the above-mentioned alkyl and alkoxy moieties, unless otherwise specified, may contain 1 to 3 carbon atoms, the enantiomers, diastereomers and geometric isomers thereof and the salts thereof, more particularly for pharmaceutical use the physiologically acceptable salts thereof with inorganic or organic acids.

Most particularly preferred compounds are those of general formula Ia wherein n, m and p each denote the number 1, $R^1$ denotes a hydrogen atom, a straight-chained or branched $C_{1-4}$-alkyl group which may be substituted by an aminocarbonyl group or, in the 2-, 3- or 4-position, by a hydroxy or alkoxy group, or a 2-propenylene group, $R^2$ denotes a hydrogen atom or a $C_{1-4}$-alkyl group, $R^3$ to $R^6$ each denote a hydrogen atom, $R^7$ denotes a phenyl group optionally substituted in the 4-position by a fluorine, chlorine or bromine atom or by a methyl, trifluoromethyl, methoxy, phenyl or nitro group, a 3,4-dichlorophenyl, 2,4-dichlorophenyl, 4-chloro-3-methylphenyl, 4-amino-3-chlorophenyl, 3,4-dimethoxyphenyl, 3,4-methylenedioxyphenyl, 4-amino-3,5-dichlorophenyl or 2-naphthyl group, and A denotes a bond, a straight-chained or branched $C_{1-5}$-alkylene group or a $C_{2-3}$-alkenylene group, wherein all the above-mentioned alkyl and alkoxy moieties, unless otherwise specified, may contain 1 to 3 carbon atoms, the enantiomers, diastereomers and geometric isomers thereof and the salts thereof, particularly for pharmaceutical use the physiologically acceptable salts thereof with inorganic or organic acids, and in particular the compounds (1) cis-O-(4-chlorobenozyl)-4-(4-dimethylaminomethylphenyl)-cyclohexanol (2) cis-O-(4-phenyl-3-butenoyl)-4-(4-dimethylaminomethylphenyl)-cyclohexanol (3) trans-O-(4-chlorophenylacetyl)-4-(4-dimethylaminomethylphenyl)-cyclohexanol (4) cis-O-(5-methylhexanoyl)-4-(4-dimethylaminomethylphenyl)-cyclohexanol (5) trans-O-(2-phenylpropionyl)-4-(4-dimethylaminomethylphenyl)-cyclohexanol (6) trans-O-(4-fluorophenylacetyl)-4-(4-dimethylaminomethylphenyl)-cyclohexanol (7) trans-O-(3,4-dichlorophenylacetyl)-4-(4-dimethylaminomethylphenyl)-cyclohexanol (8) cis-O-(4-fluorocinnamoyl)-4-(4-dimethylaminomethylphenyl)-cyclohexanol (9) trans-O-(p-tolylacetyl)-4-(4-dimethylaminomethylphenyl)-cyclohexanol

(10) trans-O-(4-[trifluoromethyl]-phenylacetyl)-4-(4-dimethylaminomethylphenyl)-cyclohexanol

(11) trans-O-(2-naphthylacetyl)-4-(4-dimethylaminomethylphenyl)-cyclohexanol

(12) trans-O-(4-nitrophenylacetyl)-4-(4-dimethylaminomethylphenyl)-cyclohexanol

(13) trans-O-(4-bromophenylacetyl)-4-(4-dimethylaminomethylphenyl)-cyclohexanol

(14) trans-O-(2,4-dichlorophenylacetyl)-4-(4-dimethylaminomethylphenyl)-cyclohexanol

(15) trans-O-([4-amino-3-chlorophenyl]acetyl)-4-(4-dimethylaminomethylphenyl)-cyclohexanol

(16) trans-O-(4-methoxyphenylacetyl)-4-(4-dimethylaminomethylphenyl)-cyclohexanol,

(17) trans-O-(4-chlorophenylacetyl)-4-(4-methylaminomethylphenyl)-cyclohexanol, and the salts thereof.

Methods of Preparation:

The compounds of formula I may be prepared, for example, by the following methods:

a) By reacting a 4-phenylcycloalkanol of general formula II

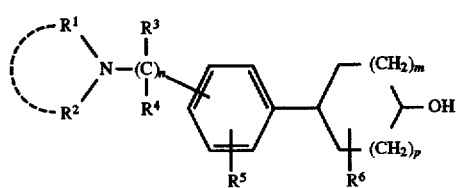

wherein n, m, p and $R^1$ to $R^6$ are as hereinbefore defined, with a carboxylic acid or the reactive derivatives thereof of general formula III $$R^7\text{—}A\text{—}COX \qquad (III)$$

wherein $R^7$ and A are as hereinbefore defined and X denotes a hydroxy group or a reactive leaving group, e.g. a halogen atom, such as a chlorine or bromine atom, a trimethylsilyloxy group, a sulphonyloxy group, e.g. the p-toluenesulphonyloxy group, an N-heteroaryl group, e.g. the 1-imidazolyl or 1-benzotriazolyl group, or an O-isourea group, e.g. the O-(N,N'-dicyclohexyl)-isourea group.

The reaction is conveniently carried out in a solvent such as benzene, toluene, xylene, diisopropylether, dioxan, tetrahydrofuran, dimethylformamide, dichloromethane or chloroform and optionally in the presence of a base such as triethylamine, pyridine or 4-dimethylaminopyridine, or in the presence of an acid, particularly if X in the general formula III denotes a hydroxy group, e.g. in the presence of boron trifluoride etherate or an acid cation exchanger at a temperature between −10° and 150° C., but preferably at a temperature between −10° and 80° C.

If the groups $R^1$ and/or $R^2$ contain free hydroxy, amino or carboxy groups, it is advisable to protect them in a suitable manner before the reaction, e.g. by converting the hydroxy into an ether group, e.g. a 2-methoxyethoxymethyl, tert.-butyl or benzylether group, the amino into a carbamate group, e.g. a trichloroethyl, 9-fluorenylmethyl or 2,4-dichlorobenzylcarbamate group and the carboxyl into an ester group, e.g. a 2,2,2-trichloroethyl, tert.-butyl or benzylester group, and cleaving the protective groups by known methods once the reaction has ended.

b) By reacting an O-acyl-4-phenylcycloalkanol of general formula IV

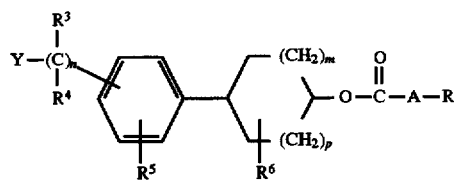

wherein n, m, p, $R^3$ to $R^7$ and A are as hereinbefore defined and Y denotes a reactive leaving group such as a halogen atom, e.g. a chlorine or bromine atom, or a sulphonyloxy group, e.g. a methylsulphonyloxy group, with an amine of general formula V

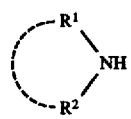

wherein $R^1$ and $R^2$ are as hereinbefore defined.

The reaction is conveniently carried out in a suitable solvent such as ethanol, tert.-butanol, dimethylformamide or tetrahydrofuran, optionally in the presence of a base such as potassium carbonate, sodium ethoxide, potassium tert.butoxide or sodium hydride, and optionally under phase transfer conditions, at a temperature between 0° and 100° C.

c) In order to prepare compounds of general formula I wherein $R^1$ is as hereinbefore defined and $R^2$ denotes a straight-chained or branched $C_{1-6}$-alkyl group which may be substituted by a hydroxy, alkoxy, alkylcarbonyloxy, alkylcarbonylamino, carboxyl, alkoxycarbonyl, aminocarbonyl or cyano group, wherein the hydroxy, alkoxy, alkylcarbonyloxy or alkylcarbonylamino group is not bound to the carbon atom in position 1: reacting an O-acyl-4-phenylcycloalkanol of general formula VI

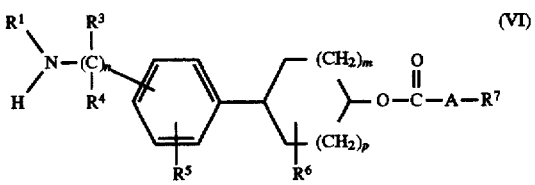

wherein n, m, p, $R^3$ to $R^7$ and A are as hereinbefore defined and Rhas the meanings given above, with a compound of general formula VII $$R^{2'}\text{—}Z^1 \qquad (VII)$$

wherein $R^{2'}$ denotes a straight-chained or branched $C_{1-6}$-alkyl group which may be substituted by a hydroxy, alkoxy, alkylcarbonyloxy, alkylcarbonylamino, carboxyl, alkoxycarbonyl, aminocarbonyl or cyano group, wherein the hydroxy, alkoxy, alkylcarbonyloxy or alkylcarbonylamino group is not bound to the carbon atom in position 1, and $Z^1$ denotes a reactive leaving group such as a halogen atom, e.g. a chlorine or bromine atom, or a sulphonyloxy group, e.g. a methylsulphonyloxy group.

The reaction is conveniently carried out in a solvent or mixture of solvents such as ethanol, tert.-butanol, tetrahydrofuran, dimethylsulphoxide or dimethylformamide, optionally in the presence of an acid binding agent, such as sodium carbonate, potassium carbonate, sodium hydroxide, sodium hydride, sodium methoxide, potassium tert.-butoxide, triethylamine or pyridine, wherein the latter two may simultaneously be used as solvent, optionally under phase transfer conditions, preferably at temperatures between 0° and 100° C., e.g. at temperatures between 20° and 50° C.

In the reactions described above, any reactive groups present such as hydroxy, amino, alkylamino, imino or carboxyl groups may be protected during the reaction by conventional protecting groups which are cleaved again once the reaction has ended.

For example, a protective group for a hydroxy group might be a trimethylsilyl, acetyl, benzoyl, methyl, ethyl, tert.-butyl, 2-methoxyethoxymethyl, benzyl or tetrahydropyranyl group, a protecting group for an amino, alkylamino or imino group might be an acetyl, benzoyl, ethoxycarbonyl or benzyl group and a protecting group for a carboxyl group might be a 2,2,2-trichloroethyl, tert.-butyl or benzylester group.

The optional subsequent cleaving of any protecting group used is preferably carried out by hydrolysis in an aqueous solvent, e.g. in water, isopropanol/water, tetrahydrofuran/water or dioxan/water, in the presence of an acid such as hydrochloric or sulphuric acid or in the presence of an alkali metal base such as sodium hydroxide or potassium hydroxide at temperatures between 0° and 100° C., preferably at the boiling temperature of the reaction mixture. However, a benzyl group is preferably cleaved by hydrogenolysis, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures between 0° and 50° C., but preferably at ambient temperature, under a hydrogen pressure of 1 to 7 bar, but preferably 3 to 5 bar.

The compounds of general formula I prepared by the above methods may be purified and isolated using known methods, e.g. crystallisation or chromatography.

In addition, the compounds of general formula I obtained may if desired be converted into the acid addition salts thereof, particularly for pharmaceutical use into the physiologically acceptable salts with inorganic or organic acids. Suitable acids include, for example, hydrochloric acid, hydrobromic acid, sulphuric acid, phosphoric acid, fumaric acid, succinic acid, lactic acid, citric acid, tartaric acid or maleic acid.

In the compounds of formula I according to the invention, stereoisomers such as diastereomers, geometric isomers or optical isomers may occur, depending on the position of the substituents on the cycloalkane ring or the form of the substituents $R^1$ to $R^7$. The invention includes both the pure stereoisomers and the mixtures thereof.

Starting Compounds:

The starting compounds of general formula II may be prepared by the following method, for example:

1. By reduction of 4-phenylcycloalkanones of general formula VIII

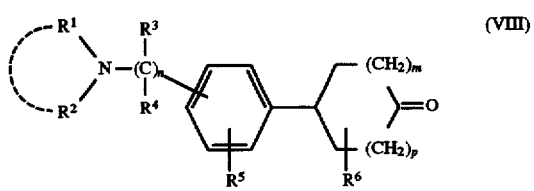

wherein n, m, p and $R^1$ to $R^6$ are as hereinbefore defined.

By a suitable choice of reducing agents, e.g. sodium borohydride or lithium tri-sec.-butyl-borohydride (L-selectrides) the reaction may be steered so as to produce mainly the e,e-isomer or the e,a-isomer of a compound of general formula II.

The ketones of general formula VIII may be prepared by known methods, e.g. by reacting monoethylene ketals of general formula IX

with an organometallic compound of general formula X

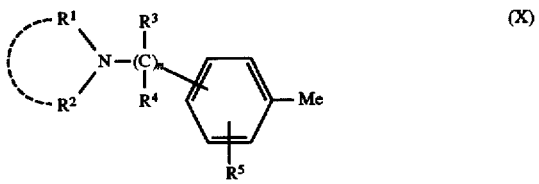

wherein n and $R^1$ to $R^5$ are as hereinbefore defined and Me denotes a lithium atom or a group —MgHal, wherein Hal is a halogen atom, preferably a chlorine atom, with subsequent cleavage using water, hydrogenation of the resulting double bond and hydrolysis of the ketal grouping.

The process may be modified so that a ketone of general formula VIII wherein $R^6$ denotes a hydrogen atom is converted, after the above reaction sequence has been carried out, into a ketone of general formula VIII wherein R denotes a $C_{1-4}$-alkyl group, e.g. by alkylation of the ketone-enolate ion.

Another method of preparing compounds of general formula VIII consists of Dieckmann cyclisation of dicarboxylic acid esters of general formula XI

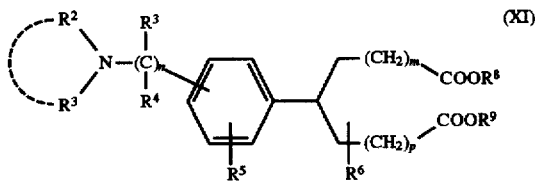

wherein n, m, p and $R^1$ to $R^6$ are as hereinbefore defined and $R^8$ and $R^9$, which may be identical or different, denote an alkyl, aralkyl or aryl group, and subsequent saponification and decarboxylation by known methods.

2. The starting compounds of general formula IV may be prepared, for example, by halomethylation of O-acyl-4-phenylcycloalkanols of general formula XII

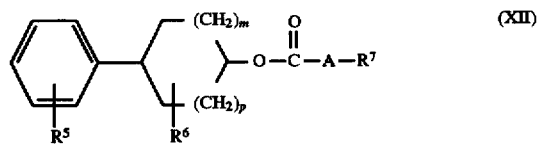

wherein m, p, $R^5$ to $R^7$ and A are as hereinbefore defined, with a corresponding aldehyde and hydrogen halide, e.g. hydrogen chloride or hydrogen bromide, in the presence of a Friedel Crafts catalyst e.g. zinc chloride, and optional subsequent replacement of the halogen atom by another suitable reactive leaving group.

3. The starting compounds of general formula VI may be prepared, for example, from O-acyl-4-phenyl-cycloalkanols of general formula XIII

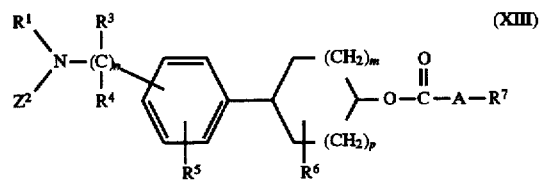

wherein n, m, p, $R^1$, $R^3$ to $R^7$ and A are as hereinbefore defined and $Z^2$ denotes a suitable protective group, by cleaving this protective group. An example of a protecting group may be a tert.-butoxycarbonyl, 1-(3,5-di-tert.-butylphenyl)-1-methylethoxycarbonyl or 2-(4-pyridyl)

ethoxycarbonyl group. The compounds of general formula XIII may be synthesised, for example, using the method described in Process 1.

The starting compounds of formulae III and V are known from the literature or may be obtained by methods known from the literature.

The compounds of general formula I have useful biological properties. They are inhibitors of cholesterol biosynthesis, particularly inhibitors of the enzyme 2,3-epoxysqualene-lanosterol-cyclase. In view of their biological properties they are particularly suitable for the treatment and prophylaxis of hyperlipidaemias, particularly, hypercholesterolaemia, hyperlipoproteinaemia and hypertriglyceridaemia and the resulting atherosclerotic vascular changes with their sequelae such as coronary heart disease, cerebral ischaemia, Claudicatio intermittens, gangrene and the like.

In order to treat these diseases the compounds of general formula I may be used either on their own in monotherapy or in conjunction with other cholesterol- or lipid-lowering substances, the compounds preferably being given orally but optionally in rectal form. Drugs which may be used in conjunction with them include, for example:

- gallic acid binding resins such as cholestramine, cholestipol and the like,
- compounds which inhibit cholesterol resorption such as sitosterol and neomycin,
- compounds which are involved in cholesterol biosynthesis, e.g. HMG-CoA-reductase inhibitors such as lovastatin, simvastatin, pravastatin and the like,
- squalene-epoxidase inhibitors such as NB 598 and analogous compounds and
- squalene-synthetase inhibitors such as, for example, compounds of the category of the isoprenoid-(phosphinylmethyl)phosphonates and squalestatin.

Other possible combinations may include the fibrates such as clofibrate, bezafibrate, gemfibrozil and the like, nicotinic acid, the derivatives and analogues thereof such as acipimox and also probucol.

The compounds of general formula I are also suitable for treating diseases connected with excessive cell proliferation. Cholesterol is an essential cell component and has to be present in sufficient quantities for cell proliferation, i.e. cell division. The inhibition of cell proliferation by inhibiting cholesterol biosynthesis is described with reference to the example of the smooth muscle cells with the HMG-CoA-reductase inhibitor of the statin type, lovastatin, as mentioned hereinbefore.

Examples of diseases connected with excessive cell proliferation include in particular tumoral diseases. In cell culture and in vivo experiments it has been shown that a reduction of the serum cholesterol or intervention in cholesterol biosynthesis by HMG-CoA-reductase inhibitors reduces tumour growth (Lancet 339, 1154–1156 [1992]). The compounds of formula I according to the invention are therefore potentially suitable for treating tumoral diseases on the basis of their inhibitory effect on cholesterol biosynthesis. They may be used on their own or to support known types of therapy.

Other examples include hyperproliferative skin diseases such as psoriasis, basal cell carcinoma, plate epithelial carcinoma, keratosis and keratinisation disorders. The term "psoriasis" used here refers to a hyperproliferative skin disease which changes the regulating mechanism of the skin. In particular, lesions are formed which constitute primary and secondary changes in proliferation in the epidermis, inflammatory skin reactions and the expression of regulatory molecules such as lymphokines and inflammatory factors. Psoriatic skin is characterised morphologically by an increased turnover of epidermis cells, thickened epidermis, abnormal keratinisation of inflammatory skin infiltrates in the dermis and polymorphonuclear leukocyte infiltration into the epidermis, leading to an increase in the basal cell cycle.

In addition, hyperkeratotic and parakeratotic cells are present. The terms "keratosis", "basal cell carcinoma", "plate epithelium carcinoma" and "keratinisation disorders" refer to hyperproliferative skin diseases in which the regulating mechanism for the proliferation and differentiation of the skin cells has been disrupted.

The compounds of formula I are effective as antagonists of skin hyperproliferation, i.e. as agents which inhibit the hyperproliferation of human keratinocytes. Consequently, they are suitable as agents for treating hyperproliferative skin diseases such as psoriasis, basal cell carcinoma, keratinisation disorders and keratosis. In order to treat these diseases the compounds of formula I may be administered either orally or topically, and may be used either on their own in form of monotherapy or in conjunction with known active substances.

Hyperproliferative vascular diseases such as stenosis and vascular occlusions based on the proliferation of smooth muscle cells, which are triggered by surgical procedures such as PTCA (percutaneous transluminal coronary angioplasty) or bypass operations may also be mentioned. As stated hereinbefore, this cell proliferation can be suppressed, as is well known, by HMG-CoA-reductase inhibitors of the statin type such as lovastatin. On the basis of their inhibitory effect on cholesterol biosynthesis, the compounds of general formula I are suitable for treatment and prophylaxis of these diseases, and may be used either on their own or in conjunction with known active substances such as intravenously administered heparin, preferably in oral forms.

Another possible use of the compounds of general formula I according to the invention is in the prevention and treatment of gallstone problems. The formation of gallstones is triggered by an unfavourable ratio of cholesterol to bile acid in the bile liquid, as a result of which the solubility of cholesterol is exceeded and cholesterol is precipitated in the form of gallstones. The effectiveness of the HMG-CoA-reductase inhibitor lovastatin in dissolving gallstones, particularly in conjunction with ursodeoxycholic acid, is described in Gastroenterology 102, No. 4, Pt.2, A319 [1992]. In view of their mode of activity the compounds of general formula I are therefore also important in the prevention and treatment of gallstone problems. They may be used either on their own or in conjunction with known therapies such as, for example, treatment with ursodeoxycholic acid or shockwave lithotripsy, and preferably administered orally.

Finally, the compounds of formula I are suitable for treating infections caused by pathogenic fungi such as *Candida albicans, Aspergillus niger, Trichophyton mentagrophytes, Penicillium sp., Cladosporium sp.* and others. As already mentioned above, the end product of sterol biosynthesis in the fungal organism is not cholesterol but ergosterol which is essential to the integrity and functioning of the fungal cell membranes. Inhibiting the biosynthesis of ergosterol therefore leads to disruption in growth and may possibly kill off the fungal organisms.

In order to treat mycoses the compounds of general formula I may be administered either orally or topically.

They may be used on their own or in conjunction with known antimycotic substances, particularly those which intervene in other stages of sterol biosynthesis, such as, for example, the squalene epoxidase inhibitors terbinafin and naftifin or the lanosterol-14α-demethylase inhibitors of the azole type such as ketoconazole and fluconazole.

Another possible use of the compounds of general formula I concerns their use in poultry rearing. Lowering the cholesterol content of eggs by administering the HMG-CoA-reductase inhibitor lovastatin to laying hens has been described (FASEB Journal 4, A 533, Abstracts 1543 [1990]). The production of low-cholesterol eggs is of importance since the cholesterol load in the body can be reduced by the use of eggs with a reduced cholesterol content without changing eating habits. In view of their inhibitory effect on cholesterol biosynthesis, the compounds of general formula I may also be used in poultry rearing to produce low cholesterol eggs, the substances preferably being given as a feed additive.

The biological effect of compounds of general formula I was determined using the following methods:

I. Measuring the Inhibition of $^{14}$C-acetate Incorporation into the Steroids which can be Precipitated with Digitonin:
Method:

Human hepatoma cells (HEP-G2) were grown for 3 days and then stimulated for 16 hours in cholesterol-free medium. The substances to be tested (dissolved in dimethylsulphoxide, final concentration 0.1%) were added during this stimulation phase. Then, after the addition of 200 μMol/l 2 -$^{14}$C-acetate, incubation is continued for a further two hours at 37° C. in an incubator.

After the cells have been removed and the sterol esters have been saponified, digitonin is added after extraction and the sterols precipitated are isolated. The $^{14}$C-acetate incorporated in the sterols capable of being precipitated by digitonin is measured by scintillation counting.

The inhibitory effect was investigated at test concentrations of $10^{-7}$ mol/l and $10^{-8}$ mol/l. It was found that the following compounds A to Q of general formula I, for example, exhibited a good inhibitory effect at these test concentrations, e.g. they showed an inhibitory effect of at least 50% at a test concentration of $10^{-8}$ mol/l:

A = cis-O-(4-chlorobenzoyl)-4-(4-dimethylaminomethylphenyl)-cyclohexanol
B = cis-O-(4-phenyl-3-butenoyl)-4-(4-dimethylaminomethylphenyl)-cyclohexanol
C = trans-O-(4-chlorophenylacetyl)-4-(4-dimethylaminomethylphenyl)-cyclohexanol
D = cis-O-(5-methylhexanoyl)-4-(4-dimethylaminomethylphenyl)-cyclohexanol
E = trans-O-(2-phenylpropionyl)-4-(4-dimethylaminomethylphenyl)-cyclohexanol
F = trans-O-(4-fluorophenylacetyl)-4-(4-dimethylaminomethylphenyl)-cyclohexanol
G = trans-O-(3,4-dichlorophenylacetyl)-4-(4-dimethylaminomethylphenyl)-cyclohexanol
H = cis-O-(4-fluorocinnamoyl)-4-(4-dimethylaminomethylphenyl)-cyclohexanol
I = trans-O-(p-tolylacetyl)-4-(4-dimethylaminomethylphenyl)-cyclohexanol
J = trans-O-(4-[trifluoromethyl]-phenylacetyl)-4-(4-dimethylaminomethylphenyl)-cyclohexanol
K = trans-O-(2-naphthylacetyl)-4-(4-dimethylaminomethylphenyl)-cyclohexanol
L = trans-O-(4-nitrophenylacetyl)-4-(4-dimethylaminomethylphenyl)-cyclohexanol
M = trans-O-(4-bromophenylacetyl)-4-(4-dimethylaminomethylphenyl)-cyclohexanol
N = trans-O-(2,4-dichlorophenylacetyl)-4-(4-dimethylaminomethylphenyl)-cyclohexanol
O = trans-O-([4-amino-3-chlorophenyl]acetyl)-4-(4-dimethylaminomethylphenyl)-cyclohexanol
P = trans-O-(4-methoxyphenylacetyl)-4-(4-dimethylaminomethylphenyl)-cyclohexanol
Q = trans-O-(4-chlorophenylacetyl)-4-(4-methylaminomethylphenyl)-cyclohexanol.

The percentages by which the above compounds inhibit $^{14}$C-acetate incorporation are given in the following Table:

| mol/l | $10^{-7}$ | $10^{-8}$ |
|---|---|---|
| A | −85 | −51 |
| B | −87 | −58 |
| C | −83 | −66 |
| D | −88 | −53 |
| E | −89 | −72 |
| F | −86 | −66 |
| G | −89 | −74 |
| H | −86 | −51 |
| I | −90 | −72 |
| J | −89 | −87 |
| K | −86 | −54 |
| L | −83 | −67 |
| M | −84 | −64 |
| N | −85 | −67 |
| O | −79 | −51 |
| P | −73 | −52 |
| Q | −79 | −50 |

As already mentioned, individual inhibitors of the enzyme 2,3-epoxysqualene-lanosterol-cyclase have already been described in the literature but they are structurally very different from the compounds of formula I according to the invention. The compounds which are most closely related in structure to the compounds of general formula I are described in EP 0 468 457. By way of a comparison, therefore, Example 1 of this publication was tested by the method described above in test concentrations of $10^{-5}$ mol/l and $10^{-6}$ mol/l. The inhibitory values of 41% and 13% obtained show that these compounds are significantly inferior to the compounds of general formula I according to the invention.

II. Measurement of the in Vivo Activity in the Rat after Oral Administration

Inhibition of the enzyme 2,3-epoxysqualene-lanosterol-cyclase brings about an increase in the 2,3-epoxysqualene levels in the liver and plasma. The quantity of 2,3-epoxysqualene formed therefore serves as a direct measurement of the potency on the animal as a whole. The measurement is carried out as follows:

Male Wistar rats (weighing 160–190 g) are given the substance, suspended in 1.5% aqueous methyl cellulose, by oesphageal tube. 5 hours after administration, blood is taken retroorbitally from the venus plexus. Plasma is worked up using the method of Bligh and Dyer (Canad. J. Biochem. Physiol. 37, 912, [1959]), purified using a preliminary column and then analysed with HPLC. The peaks obtained are identified and quantified using calibrating substances. An internal standard is used to test the reproducibility of the results.

The tests were carried out with concentrations of 0.1 and 1.0 mg/kg. In the Table which follows, the test data of the above-mentioned substances B, C, J, M, N and P are shown, by way of example, for the 2,3-epoxysqualene levels obtained in rat plasma. No measurable 2,3-epoxysqualene levels occur under the test conditions in the control animals.

2,3-Epoxysqualene Levels in Plasma (Rat)

| Substance | 2,3-Epoxysqualene [µg/ml] | |
|---|---|---|
| | 0.1 mg/kg | 1.0 mg/kg |
| B | 0.4 | 1.1 |
| C | 0.6 | 4.2 |
| J | 0.5 | 3.6 |
| M | 0.6 | 3.5 |
| N | 0.1 | 2.2 |
| P | 0.3 | 0.9 |

None of the inhibitors of the enzyme 2,3-epoxysqualene-lanosterol-cyclase described in the literature has hitherto been found to inhibit cholesterol biosynthesis in the whole animal.

The compounds prove totally non-toxic at the curative dose. For example, compound C shows no side effects in the rat, and compounds J and M show no side effects in the mouse, after oral administration of 100 mg/kg once a day for 5 days.

For pharmaceutical use the compounds of general formula I may be incorporated in the usual pharmaceutical preparations for oral and topical administration in a manner known per se.

Formulations for oral use include, for example, plain or coated tablets and capsules whilst suppositories are preferably used for rectal administration.

Topical formulations include gels, creams, lotions, ointments, powders, aerosols and other conventional preparations for using therapeutic agents on the skin. The quantity of active substance for topical use is 1 to 50 mg per gram of preparation but preferably 5 to 20 mg per gram of preparation. As well as being used on the skin the topical formulations according to the invention may also be used in the treatment of mucosa which are accessible for topical treatment. For example, the topical formulations may be applied to the mucosa of the mouth, lower colon and elsewhere.

The oral or rectal daily dose is between 1 and 1200 mg for a person weighing 60 kg, but preferably the daily dose is from 5 to 100 mg for a person weighing 60 kg. The daily dose is preferably divided into 1 to 3 individual doses.

For topical use the compounds are administered in preparations containing about 1 to 1000 mg, more particularly 10 to 300 mg of active substance per day. The daily dose is preferably divided into 1 to 3 individual doses.

For use in poultry rearing in order to produce low cholesterol eggs, the active substances of general formula I are given to the animals in the form of an additive to their feed by normal methods. The concentration of active substances in the complete feed is normally 0.01 to 1%, but preferably 0.05 to 0.5%.

The active substances may be added to the feed as such. Thus, the feedstuffs according to the invention for laying hens will contain, apart from the active substance and possibly a conventional vitamin/mineral mixture, maize, soya flour, meatmeal, edible fat and soya oil, for example. One of the above-mentioned compounds of formula I is added to this feedstuff as an active substance in a concentration of 0.01 to 1%, but preferably 0.05 to 0.5%.

The Examples which follow are intended to illustrate the invention:

In the following Examples the thin layer chromatography was carried out using ready-made TLC plates produced by Messrs. E. Merck of Darmstadt, the plates being specifically:

a) silica gel 60 $F_{254}$ b) aluminium oxide $F_{254}$ (Type E)

Preparation of the Starting Compounds

EXAMPLE I

4-(4-Dimethylaminomethylphenyl)-cyclohexanone a) 4-(4-Dimethylaminomethylphenyl)-4-hydroxycyclohexanone-ethylene ketal

To a solution of 36.4 g (0.17 mol) of 4-bromo-N,N-dimethylbenzylamine in 250 ml of dry tetrahydrofuran, cooled to −70° C., are added dropwise, under a nitrogen atmosphere and with stirring, 112 ml (0.179 mol) of a 1.6 molar solution of n-butyllithium in hexane in such a way that the temperature does not exceed −65° C. The orange solution is stirred for a further 15 minutes at −70° C. and then within 10 minutes a solution of 27.6 g (0.172 mol) of 1,4-cyclohexanedione-monoethylene ketal in 110 ml of tetrahydrofuran is added, whilst the temperature must not exceed −65° C.

The reaction mixture is stirred first for 30 minutes at −70° C. and then without external cooling until a temperature of +20° C. is reached, then poured into 600 ml of ice water and extracted with 200 ml of ethyl acetate. The organic phase is separated off and the aqueous phase is extracted several times with ethyl acetate. The combined organic extracts are dried with sodium sulphate, evaporated down in vacuo and the residue remaining is recrystallised from diisopropylether. 41.9 g (85% of theory) of 4-(4-dimethylaminomethylphenyl)-4-hydroxycyclohexanone-ethylene ketal are obtained, m.p. 84°–86° C.

b) 1-(4-Dimethylaminomethyl)phenyl-4-ethylenedioxy-1-cyclohexene

A mixture of 22.4 g (0.077 mol) of 4-(4-dimethylaminomethyl-phenyl)-4-hydroxycyclohexanone-ethylene ketal, 15.0 g (0.079 mol) of p-toluenesulphonic acid monohydrate, 39 ml of ethylene glycol and 240 ml of toluene is refluxed for 3½ hours with stirring and the reaction water produced is continuously removed. The cooled reaction mixture is poured into 200 ml of water and adjusted to pH 12–13 with 2N NaOH. The organic phase is separated off and the aqueous phase is extracted several times with toluene. The combined organic extracts are dried with sodium sulphate and evaporated down in vacuo. 21 g (about 100%) of the title compound are obtained in the form of a yellow oil.

c) 1-(4-Dimethylaminomethyl)phenyl-4-ethylenedioxy-1-cyclohexane

A solution of 21 g (0.077 mol) of crude 1-(4-dimethylaminomethyl)phenyl-4-ethylenedioxy-1-cyclohexene in 200 ml of ethyl acetate and 100 ml of methanol is combined with 5 g of palladium/barium sulphate catalyst and hydrogenated for 1.5 hours under a hydrogen pressure of 5 bar. After the catalyst has been removed the residue is evaporated down in vacuo. 20 g (about 100%) of the title compound are obtained as a yellowish-brown oil.

d) 4-(4-Dimethylaminomethyl)phenyl-cyclohexanone

A mixture of 20 g (0.077 mol) of crude 1-(4-dimethylaminomethyl)phenyl-4-ethylenedioxy-1-cyclohexane and 110 ml of 2N hydrochloric acid is stirred for 3.5 hours at ambient temperature. The aqueous solution formed is extracted several times with ethyl acetate; the organic extracts are discarded. The aqueous phase is adjusted to pH 13–14 with 50% sodium hydroxide solution whilst being cooled and is extracted several times with ethyl acetate. The combined organic extracts are washed with saturated sodium chloride solution, dried with sodium sulphate and evaporated down in vacuo. 14 g (79% of theory) of 4-(4-dimethylaminomethyl)phenyl-cyclohexanone are obtained, melting point 64°–67° C., as a light yellow product. An analytical sample is recrystallised from petroleum ether 60/90.

|  | Melting point: 65–67° C. $C_{15}H_{21}NO$ (231.34) | | |
|---|---|---|---|
| Calculated: | C 77.88 | H 9.15 | N 6.05 |
| Found: | 77.69 | 9.32 | 5.98 |

EXAMPLE II trans-4-(4-Dimethylaminomethylphenyl)-cyclohexanol

To a solution of 11.1 g (0.048 mol) of 4-(4-dimethylaminomethylphenyl)-cyclohexanone in 100 ml of absolute methanol, which has been cooled to –10° C., is added 1.82 g (0.048 mol) of sodium borohydride in batches with stirring. The reaction mixture is allowed to react for 1.5 hours at ambient temperature and then evaporated down in vacuo. The residue remaining is mixed with water, acidified with concentrated hydrochloric acid, stirred for 30 minutes at ambient temperature, made alkaline with 50% sodium hydroxide solution and extracted several times with chloroform. The combined extracts are dried with sodium sulphate and evaporated down in vacuo. The residue remaining, which consists of a mixture of trans/cis-4-(4-dimethylaminomethyl-phenyl)-cyclohexanol (cis fraction <10%) is purified by column chromatography (aluminium oxide neutral, activity stage III, ICN; petroleum ether/methylethyl ketone=5:1). White crystals are obtained, melting point 63°–65° C.

|  | Yield: 8.8 g (79% of theory), $C_{15}H_{23}NO$ (233.36) | | |
|---|---|---|---|
| Calculated: | C 77.21 | H 9.93 | N 6.00 |
| Found: | 77.34 | 10.02 | 5.89 |

EXAMPLE III cis-4-(4-Dimethylaminomethylphenyl)-cyclohexanol 50 ml (0.05 mol) of a 1 molar solution of lithium tri-sec.-butyl-borohydride in absolute tetrahydrofuran are diluted with 100 ml of absolute tetrahydrofuran under a nitrogen atmosphere and then, at –65° C. to –70° C., with stirring and within 10 minutes, a solution of 5.8 g (0.025 mol) of 4-(4-dimethylaminomethylphenyl)-cyclohexanone in 50 ml of absolute tetrahydrofuran is added thereto. The reaction mixture is then left to react for 3 hours at –70° C. and then heated to ambient temperature within 1 hour. It is then hydrolysed with 20 ml of 75% aqueous ethanol and the organoborane is oxidised with alkaline hydrogen peroxide (10 ml of 6M NaOH/15 ml 30% $H_2O_2$). The organic phase is separated off, the aqueous phase is saturated with potassium carbonate and extracted with 50 ml of ethyl acetate. The combined organic extracts are dried with sodium sulphate and evaporated down in vacuo. The greasy residue remaining, which consists of a mixture of cis/trans-4-(4-dimethylaminomethylphenyl)cyclohexanol (trans fraction <5%) is purified by column chromatography (aluminium oxide neutral, activity stage III, ICN; petroleum ether/methylethyl ketone=5:1).

The product is obtained as a colourless oil.

Yield: 4.1 g (71% of theory). $^1$H-NMR spectrum (200 MHz, $CDCl_3$); signals at ppm: 1.5–2.0 (2m,8H); 2.25 (s,6H); 2.4–2.65 (m, 1H); 3.4 (s,2H); 4.1–4.18 (m, 1H); 7.15–7.3 (m,4H).

EXAMPLE IV trans-O-Acetyl-4-(4-chloromethylphenyl)-cyclohexanol a) 4-Phenylcyclohexanol

To a solution of 31.4 g (0.18 mol) of 4-phenylcyclohexanone in 500 ml of absolute methanol, which is cooled to –10° C., are added 6.8 g (0.18 mol) of sodium borohydride in batches with stirring. The reaction mixture is allowed to react for 0.5 hours at –10° C. and for 3 hours at ambient temperature and then evaporated down in vacuo. The residue remaining is mixed with water and acidified with 2N hydrochloric acid. The suspension formed is stirred for 1 hour and the crystalline product is suction filtered, dried and recrystallised from diisopropylether. 21 g (66% of theory) of 4-phenylcyclohexanol are obtained, melting point: 112°–114° C.

b) O-Acetyl-4-phenylcyclohexanol

To a mixture of 20.3 g (0.115 mol) of 4-phenylcyclohexanol, 14.2 ml (0.15 mol) of acetanhydride and 29 ml of triethylamine are added, with stirring and at ambient temperature, 2.3 g (0.02 mol) of 4-dimethylaminopyridine, a clear solution being produced in an exothermic reaction. This is heated to 80° C. for 3 hours and the reaction mixture is then poured into ice water. The crystalline product precipitated is suction filtered, dissolved in ether, washed with sodium bicarbonate solution, dried and evaporated down in vacuo. 23 g (92% of theory) of O-acetyl-4-phenylcyclohexanol are obtained. The product is obtained initially as an oil but crystallises when left to stand.

Melting point: 43°–45° C.

c) trans-O-Acetyl-4-(4-chloromethylphenyl)-cyclohexanol

A solution of 24.3 g (0.11 mol) of O-acetyl-4-phenylcyclohexanol in 1300 ml of methylene chloride is combined with 26.0 g (0.86 mol) of paraformaldehyde and 26.0 g (0.19 mol) of zinc chloride. Hydrogen chloride is introduced into this suspension, with stirring, for 2.5 hours, whilst the temperature rises to about 30° C. and a substantially homogeneous solution is formed. The mixture is then allowed to react for 15 hours at ambient temperature and the reaction mixture is then hydrolysed with stirring in about 1.5 litres of ice water. The organic phase is separated off, the aqueous phase is extracted with methylene chloride again and the two organic phases are combined. They are washed until neutral, dried and evaporated in vacuo. The yellow oil remaining is crystallised by trituration with diisopropylether and the solid product is recrystallised from diisopropylether. White crystals are obtained, melting point 87°–89° C.

| Yield: 12.7 g (43% of theory). C₁₅H₁₉ClO₂ (266.77) | | | |
|---|---|---|---|
| Calculated: | C 67.53 | H 7.18 | Cl 13.29 |
| Found: | 67.68 | 7.29 | 13.11 |

EXAMPLE V cis/trans-O-(4-Chlorophenylacetyl)-4-(4-N-[tert.-butoxycarbonyl]-methylaminomethyl)phenyl-cyclohexanol a) 4-(4-Methylaminomethyl)phenyl-4-hydroxycyclohexanone-ethylene ketal

A solution of 94 g (0.47 mol) of 4-bromo-(N-methyl)-benzylamine in 460 ml of dry tetrahydrofuran is combined first with 300 ml (0.48 mol) of a 1.6 molar solution of n-butyl lithium in hexane and then with 52.5 g (0.48 mol) of trimethylchlorosilane, under a nitrogen atmosphere and at to −25° C. The reaction mixture is stirred for a further 15 minutes at this temperature and then cooled to −75° C. Then another 320 ml (0.51 mol) of a 1.6 molar solution of n-butyllithium in hexane are added so that the temperature does not exceed −70° C. The mixture is stirred for a further 20 minutes at −75° C. and then, within 20 minutes, mixed with a solution of 76 g (0.47 mol) of 1,4-cyclohexanedione-monoethylene ketal in 200 ml of tetrahydrofuran, whilst the temperature should not exceed −65° C. The reaction mixture is then stirred first for 30 minutes at −70° C. and then without external cooling until a temperature of +20° C. is reached. It is then decomposed in ice cold aqueous ammonium chloride solution and extracted several times with methylene chloride. The combined organic extracts are dried with sodium sulphate, the solvent is eliminated and the residue remaining is recrystallised from diisopropylether. 77 g (59% of theory) of 4-(4-methylaminomethyl)phenyl-4-hydroxycyclohexanone-ethylene ketal are obtained, melting point 95°–97° C.

b) 1-(4-Methylaminomethyl)phenyl-4-ethylenedioxy-1-cylohexene

A mixture of 68 α (0.24 mol) of 4-(4-methylaminomethylphenyl)phenyl-4-hydroxycyclohexanone-ethylene ketal, 51 g (0.27 mol) of p-toluenesulphonic acid monohydrate, 150 ml of ethylene glycol and 900 ml of toluene is refluxed for 2.5 hours with stirring and the reaction water formed is continuously removed. The cooled reaction mixture is made alkaline with 1N sodium hydroxide solution (pH 12–13), the organic phase is separated off and the aqueous phase is extracted several times with ethyl acetate. The combined organic phases are dried with sodium sulphate and evaporated down in vacuo. 63 g (about 100% of theory) of 1-(4-methylaminomethyl)phenyl-4-ethylenedioxy-1-cyclohexene are obtained as a yellowish oil.

c) 1-(4-N-[tert.-Butoxycarbonyl]-methylaminomethyl)phenyl-4-ethylenedioxy-1-cyclohexene A solution of 63 g (0.24 mol) of the crude 1-(4-methylaminomethyl)phenyl-4-ethylenedioxy-1-cyclohexene in 350 ml of absolute tetrahydrofuran is combined, with stirring, with a solution of 58 g (0.26 mol) of di-tert.-butyldicarbonate in 100 ml of absolute tetrahydrofuran, the temperature being maintained at between 15 and 20° C. by cooling. After the development of $CO_2$ has died away, the mixture is left for a further 10 hours at ambient temperature, the solvent is distilled off in vacuo, the residue is mixed with water and extracted several times with ether. After drying with sodium sulphate and evaporation 84 g (about 100% of theory) of 1-(4-N-[tert.-butoxycarbonyl]-methylaminomethyl)phenyl-4-ethylenedioxy-1-cyclohexene are obtained as a yellowish oil.

d) 4-(4-N-[tert. -Butoxycarbonyl]-methylaminomethyl)phenyl-cyclohexanone

A solution of 84 g (0.24 mol) of the crude 1-(4-N-[tert.-butoxycarbonyl]-methylaminomethyl)phenyl-4-ethylenedioxy-1-cyclohexene in methanol/ethyl acetate (250+250 ml) is combined with 10 g of palladium/barium sulphate catalyst and hydrogenated for 4 hours at ambient temperature under a hydrogen pressure of 3 bar. The catalyst is separated off, the solvent is distilled off in vacuo, the oily residue is dissolved in acetone/water (1400+140 ml), and after the addition of 8.5 g (0.034 mol) of pyridinium tosylate, it is refluxed for 15 hours. The solvent is then distilled off in vacuo, the residue is combined with water and extracted several times with methylene chloride. After the organic phase has been dried with sodium sulphate and evaporated down, 61 g (77% of theory) of 4-(4-N-[tert.-butoxycarbonyl]-methylaminomethyl)phenyl-cyclohexanone are obtained as a pale yellow oil which solidifies when left to stand for a length of time.

Melting point: 55°–57° C.

e) 4-(4-N-[tert.-Butoxycarbonyl]-methylaminomethyl)phenyl-cyclohexanol (cis/trans mixture)

1.31 g (0.035 mol) of sodium borohydride is added in batches, with stirring, to a solution of 11 g (0.035 mol) of 4-(4-N-[tert.-butoxycarbonyl]-methylaminomethyl)phenyl-cyclohexanone in 70 ml of absolute methanol, cooled to −10° C. The reaction mixture is allowed to react for 0.5 hours at −10° C. and for 2 hours at ambient temperature and then evaporated down in vacuo. The residue remaining is mixed with water and stirred for 1 hour at ambient temperature. The solid product produced is suction filtered, dissolved in ethyl acetate and this solution is dried over sodium sulphate. After evaporation in vacuo, 8.6 g (77% of theory) of a mixture of the cis- and trans-forms of 4-(4-N-[tert.-butoxycarbonyl]-methylaminomethyl)phenyl-cyclohexanol are left in the form of a colourless oil. This can be separated into the pure isomers by column chromatography (aluminium oxide neutral, activity stage III, ICN; petroleum ether/ethyl acetate=3:1).

$R_f$ value (aluminium oxide; petroleum ether/ethyl acetate=3:1): 0.21 (trans) and 0.31 (cis).

f) O-(4-Chlorophenylacetyl)-4-(4-N-[tert.-butoxycarbonyl]-methylaminomethyl)phenyl-cyclohexanol (cis/trans mixture)

A mixture of 0.54 g (0.0032 mol) of 4-chlorophenylacetic acid, 0.52 g (0.0032 mol) of N,N'-carbonyldiimidazole and 20 ml of xylene is heated to 60° C. for 1 hour with stirring. Then a solution of 0.85 g (0.0027 mol) of 4-(4-N-[tert.-butoxycarbonyl]-methylaminomethyl)phenyl-cyclohexanol (cis/trans mixture) in 10 ml of xylene is added and the reaction mixture is heated to 160° C. for a further 8 hours. After cooling, it is evaporated down in vacuo, the residue is mixed with water and extracted with ethyl acetate. The organic phase is dried over sodium sulphate and evaporated down in vacuo. 1.3 g (about 100% of theory) of O-(4-chlorophenylacetyl)-4-(4-N-[tert.-butoxycarbonyl]-methylaminomethyl)phenyl-cyclohexanol (cis/trans mixture) are left as a reddish-brown oil.

$R_f$ value (aluminium oxide; petroleum ether/ethyl acetate=3:1): 0.78 (trans) and 0.85 (cis).

The following substance was synthesised analogously:

(1) trans-O-(4-chlorophenylacetyl)-4-(4-N-[tert.-butoxycarbonyl]-methylaminomethyl)phenyl-cyclohexanol from trans-4-(4-N-[tert.-butoxycarbonyl]-methylaminomethyl)-phenyl-cyclohexanol and 4-chlorophenylacetic acid/N,N'-carbonyldiimidazole. White crystals.

Melting point: 94°–96° C.

Preparation of the End Products:

EXAMPLE 1 trans-O-(4-Chlorobenzoyl)-4-(4-dimethylaminomethylphenyl)-cyclohexanol

A solution of 1.0 g (0.0043 mol) of trans-4-(4-dimethylaminomethylphenyl)-cyclohexanol and 0.6 ml of triethylamine in 50 ml of methylene chloride is combined, dropwise, with 0.75 g (0.0043 mol) of 4-chlorobenzoylchloride, with stirring, and refluxed for 3 hours. After cooling, 50 ml of water are added, the mixture is adjusted to pH 12–13 with sodium hydroxide solution, the methylene chloride phase is separated off and the aqueous phase is extracted once more with methylene chloride. The combined organic phases are dried over sodium sulphate and evaporated down in vacuo. The solid residue is purified by column chromatography (aluminium oxide neutral, activity stage III, ICN; petroleum ether/ethyl acetate=40:1). White crystals are obtained with a melting point of 94°–95° C.

Yield: 1.1 g (69% of theory) $^1$H-NMR spectrum (200 MHz, CDCl$_3$); signals at ppm: 1.55–1.8 (m,4H); 1.9–2.1 (m,2H); 2.15–2.3 (s+m,6+2H); 2.5–2.7 (m,1H); 3.4 (s,2H); 4.9–5.1 (m,1H); 7.15–7.3 (m,4H); 7.4 (d,2H); 8.0 (d,2H).

The following substances were synthesised analogously:

(1) trans-O-acetyl-4-(4-dimethylaminomethylphenyl)-cyclohexanol from trans-4-(4-dimethylaminomethylphenyl)-cyclohexanol and acetylchloride/triethylamine. Colourless syrup.

$^1$H-NMR spectrum (200 MHz, CDCl$_3$); signals at ppm: 1.45–1.7 (m,4H); 1.9–2.05 (m,2H); 2.05–2.15 (s+m,3+2H); 2.23 (s,6H); 2.4–2.65 (m,1H); 3.4 (s,2H); 4.7–4.9 (m, 1H); 7.1–7.3 (m,4H).

(2) trans-O-butyryl-4-(4-dimethylaminomethylphenyl)-cyclohexanol from trans-4-(4-dimethylaminomethylphenyl)-cyclohexanol and butyric acid chloride/triethylamine. Colourless oil.

$^1$H-NMR spectrum (200 MHz, CDCl$_3$); signals at ppm: 0.9–1.02 (t,3H); 1.45–1.75 (m,6H); 1.89–2.05 (m,2H); 2.05–2.18 (m,2H); 2.18–2.38 (s+t,6+2H); 2.4–2.6 (m, 1H); 3.4 (s,2H); 4.7–4.9 (m, 1H); 7.1–7.3 (m,4H).

(3) trans-O-cyclopropanoyl-4-(4-dimethylaminomethylphenyl)-cyclohexanol from trans-4-(4-dimethylaminomethylphenyl)-cyclohexanol and cyclopropane carboxylic acid chloride/triethylamine. Colourless wax.

$^1$H-NMR spectrum (200 MHz, CDCl$_3$); signals at ppm: 0.81–0.87 (m,2H); 0.95–1.02 (m,2H); 1.45–1.7 (m,4H); 1.9–2.0 (m,2H); 2.05–2.15 (m,2H); 2.24 (s,6H); 2.4–2.63 (2m,2H); 3.4 (s, 2H); 4.73–4.83 (m, 1H); 7.12–7.25 (m, 4H).

(4) trans-O-cyclohexanoyl-4-(4-dimethylaminomethylphenyl)-cyclohexanol from trans-4-(4-dimethylaminomethylphenyl)-cyclohexanol and cyclohexane carboxylic acid chloride/triethylamine. White crystals.

Melting point: 66°–68° C.

(5) cis-O-(4-chlorophenylacetyl)-4-(4-dimethylaminomethylphenyl)-cyclohexanol from cis-4-(4-dimethylaminomethylphenyl)-cyclohexanol and 1-chlorophenylacetylchloride/triethylamine. Colourless oil.

$^1$H-NMR spectrum (200 MHz, CDCl$_3$); signals at ppm: 1.5–1.75 (m,6H); 1.88–2.05 (m,2H); 2.25 (s,6H); 2.4–2.65 (m, 1H); 3.4 (s,2H); 3.65 (s,2H); 5.05–5.15 (m, 1H); 7.08 (d, 2H), 7.2–7.4 (m, 6H).

(6) trans-O-(4-phenyl-3-butenoyl)-4-(4-dimethylaminomethylphenyl)-cyclohexanol from trans-4-(4-dimethylaminomethylphenyl)-cyclohexanol and 4-phenyl-3-butenoic acid chloride/triethylamine. White crystals.

Melting point: 90°–91° C.

(7) cis-O-(4-phenyl-3-butenoyl)-4-(4-dimethylaminomethylphenyl)-cyclohexanol from cis-4-(4-dimethylaminomethylphenyl)-cyclohexanol and 4-phenyl-3-butenoic acid chloride/triethylamine. White crystals.

Melting point: 71°–73° C.

EXAMPLE 2 trans-O-(4-Chlorophenylacetyl)-4-(4-dimethylaminomethylphenyl)-cyclohexanol

To a mixture of 0.43 g (0.0025 Mol) of 4-chlorophenylacetic acid and 30 ml of xylene are added 0.41 g (0.0025 Mol) of N,N'-carbonyldiimidazole, a white product being produced with the release of CO$_2$. The reaction mixture is heated to 60° C. for 1 hour with stirring and then 0.5 g (0.0021 mol) of trans-4-(4-dimethylaminomethylphenyl)-cyclohexanol are added. The mixture is heated to 160° C. for 12 hours with stirring, cooled to ambient temperature, mixed with water and adjusted to pH 12–13 using 2N sodium hydroxide solution. The xylene phase is separated off, the aqueous phase is extracted several times with ethyl acetate, the organic phases are combined, dried and evaporated down in vacuo. The solid residue is purified by column chromatography (aluminium oxide basic, activity stage III, ICN; petroleum ether/ethyl acetate=10:1). White crystals are obtained with a melting point of 75°–77° C.

Yield: 0.7 g (86% of theory). $^1$H-NMR spectrum (200 MHz, CDCl$_3$); signals at ppm: 1.4–1.7 (m,4H); 1.8–2.15 (m,4H); 2.25 (s,6H); 2.4–2.6 (m,1H); 3.38 (s,2H); 3.6 (s,2H); 4.7–4.9 (m, 1H); 7.1–7.35 (m,8H).

The following substances were synthesised analogously:

(1) trans-O-(5-methylhexanoyl)-4-(4-dimethylaminomethylphenyl)-cyclohexanol from trans-4-(4-dimethylaminomethylphenyl)-cyclohexanol and 5-methylhexanoic acid/N,N'-carbonyldiimidazole. White crystals.

Melting point: 35°–36° C.

(2) cis-O-(5-methylhexanoyl)-4-(4-dimethylaminomethylphenyl)-cyclohexanol from cis-4-(4-dimethylaminomethylphenyl)-cyclohexanol and 5-methylhexanoic acid/N,N'-carbonyldiimidazole. Colourless oil.

¹H-NMR spectrum (200 MHz, CDCl₃); signals at ppm: 0.9 (d, 6H); 1.15–1.32 (m, 2H); 1.5–1.88 (m, 9H); 1.95–2.1 (m,2H); 2.25 (s,6H); 2.3 (d,2H); 2.48–2.69 (m, 1H); 3.4 (s, 2H); 5.08–5.18 (m, 1H); 7.12–7.3 (m, 4H).

(3) trans-O-cyclohexylacetyl-4-(4-dimethylaminomethylphenyl)-cyclohexanol from trans-4-(4-dimethylaminomethylphenyl)-cyclohexanol and cyclohexylacetic acid/N,N'-carbonyldiimidazole White crystals.

Melting point: 37°–39° C.

(4) trans-O-(2-butenoyl)-4-(4-dimethylaminomethylphenyl)-cyclohexanol from trans-4-(4-dimethylaminomethylphenyl)-cyclohexanol and crotonic acid/N,N'-carbonyldiimidazole White crystals.

Melting point: 69°–71° C.

(5) trans-O-(2-hexenoyl)-4-(4-dimethylaminomethylphenyl)-cyclohexanol from trans-4-(4-dimethylaminomethylphenyl)-cyclohexanol and 2-hexenoic acid/N,N'-carbonyldiimidazole. White crystals.

Melting point: 40°–42° C.

(6) trans-O-(3-cyclohexylpropenoyl)-4-(4-dimethylaminomethylphenyl)-cyclohexanol from trans-4-(4-dimethylaminomethylphenyl)-cyclohexanol and 3-cyclohexylpropenoic acid/N,N'-carbonyldiimidazole. White crystals.

Melting point: 46°–47° C.

(7) trans-O-benzoyl-4-(4-dimethylaminomethylphenyl)-cyclohexanol from trans-4-(4-dimethylaminomethylphenyl)-cyclohexanol and benzoic acid/N,N'-carbonyldiimidazole. White crystals.

Melting point: 68°–70° C.

(8) trans-O-(4-chloro-3-methylbenzoyl)-4-(4-dimethylaminomethylphenyl)-cyclohexanol from trans-4-(4-dimethylaminomethylphenyl)-cyclohexanol and 4-chloro-3-methylbenzoic acid/N,N'-carbonyldiimidazole. White crystals.

Melting point: 100°–102° C.

(9) trans-O-(2-naphthoyl)-4-(4-dimethylaminomethylphenyl)-cyclohexanol from trans-4-(4-dimethylaminomethylphenyl)-cyclohexanol and 1-naphthoic acid/N,N'-carbonyldiimidazole. White crystals.

Melting point: 110°–112° C.

(10) trans-O-phenylacetyl-4-(4-dimethylaminomethylphenyl)-cyclohexanol from trans-4-(4-dimethylaminomethylphenyl)-cyclohexanol and phenylacetic acid/N,N'-carbonyldiimidazole. White crystal.

Melting point: 38°–40° C.

(11) trans-O-(4-fluorophenylacetyl)-4-(4-dimethylaminomethylphenyl)-cyclohexanol from trans-4-(4-dimethylaminomethylphenyl)-cyclohexanol and 4-fluorophenylacetic acid/N,N'-carbonyldiimidazole. White crystals.

Melting point: 68°–70° C.

(12) cis-O-(4-fluorophenylacetyl)-4-(4-dimethylaminomethylphenyl)-cyclohexanol from cis-4-(4-dimethylaminomethylphenyl)-cyclohexanol and 4-fluorophenylacetic acid/N,N'-carbonyldiimidazole. Colourless oil.

¹H-NMR spectrum (200 MHz, CDCl₃); signals at ppm: 1.5–1.75 (m,6H); 1.85–2.05 (m,2H); 2.3 (s,6H); 2.4–2.65 (m, 1H); 3.43 (s,2H); 3.65 (s,2H); 5.05–5.15 (m, 1H); 7.0–7.15 (m,4H); 7.2–7.38 (m,4H).

(13) trans-O-(4-bromophenylacetyl)-4-(4-dimethylaminomethylphenyl)-cyclohexanol from trans-4-(4-dimethylaminomethylphenyl)-cyclohexanol and 4-bromophenylacetic acid/N,N'-carbonyldiimidazole. White crystals.

Melting point: 72°–74° C.

(14) trans-O-(3,4-dichlorophenylacetyl)-4-(4-dimethylaminomethylphenyl)-cyclohexanol from trans-4-(4-dimethylaminomethylphenyl)-cyclohexanol and 3,4-dichlorophenylacetic acid/N,N'-carbonyldiimidazole. White crystals.

Melting point: 95°–97° C.

(15) cis-O-(3,4-dichlorophenylacetyl)-4-(4-dimethylaminomethylphenyl)-cyclohexanol from cis-4-(4-dimethylaminomethylphenyl)-cyclohexanol and 3,4-dichlorophenylacetic acid/N,N'-carbonyldiimidazole. Colourless oil.

¹H-NMR spectrum (200 MHz, CDCl₃); signals at ppm: 1.5–1.75 (m,6H); 1.9–2.05 (m,2H); 2.28 (s,6H); 2.4–2.65 (m, 1H); 3.4 (s,2H); 3.62 (s,2H); 5.8–5.17 (m, 1H); 7.05–7.3 (m, 5H); 7.35–7.49 (m, 2H).

(16) trans-O-(2,4-dichlorophenylacetyl)-4-(4-dimethylaminomethylphenyl)-cyclohexanol from trans-4-(4-dimethylaminomethylphenyl)-cyclohexanol and 2,4-dichlorophenylacetic acid/N,N'-carbonyldiimidazole. White crystals.

Melting point: 78°–80° C.

(17) trans-O-(p-tolylacetyl)-4-(4-dimethylaminomethylphenyl)-cyclohexanol from trans-4-(4-dimethylaminomethylphenyl)-cyclohexanol and p-tolylacetic acid/N,N'-carbonyldiimidazole. White crystals.

Melting point: 40°–42° C.

(18) trans-O-(4-[trifluoromethyl]-phenylacetyl)-4-(4-dimethylaminomethylphenyl)-cyclohexanol from trans-4-(4-dimethylaminomethylphenyl)-cyclohexanol and 4-(trifluoromethyl)-phenylacetic acid/N,N'-carbonyldiimidazole. White crystals.

Melting point: 73°–75° C.

(19) trans-O-(4-methoxyphenylacetyl)-4-(4-dimethylaminomethylphenyl)-cyclohexanol from trans-4-(4-dimethylaminomethylphenyl)-cyclohexanol and 4-methoxyphenylacetic acid/N,N'-carbonyldiimidazole. White crystals.

Melting point: 47°–49° C.

(20) trans-O-(4-nitrophenylacetyl)-4-(4-dimethylaminomethylphenyl)-cyclohexanol from trans-4-(4-dimethylaminomethylphenyl)-cyclohexanol and 4-nitrophenylacetic acid/N,N'-carbonyldiimidazole. Yellowish crystals.

Melting point: 136°–137° C.

(21) trans-O-[3-(4-fluorophenyl)-propionyl]-4-(4-dimethylaminomethylphenyl)-cyclohexanol from trans-4-(4-dimethylaminomethylphenyl)-cyclohexanol and 3-(4-fluorophenyl)-propionic acid/N,N'-carbonyldiimidazole. White crystals.

Melting point: 58°–59° C.

(22) trans-O-[3-(4-chlorophenyl)-propionyl]-4-(4-dimethylaminomethylphenyl)-cyclohexanol from trans-4-(4-dimethylaminomethylphenyl)-cyclohexanol and 3-(4-chlorophenyl)-propionic acid/N,N'-carbonyldiimidazole. White crystals.

Melting point: 85°–87° C.

(23) trans-O-(4-biphenylacetyl)-4-(4-dimethylaminomethylphenyl)-cyclohexanol from trans-4-(4-dimethylaminomethylphenyl)-cyclohexanol and 4-biphenylacetic acid/N,N'-carbonyldiimidazole. White crystals.

Melting point: 88°–89° C.

(24) trans-O-(2-naphthylacetyl)-4-(4-dimethylaminomethylphenyl)-cyclohexanol from trans-4-(4-dimethylaminomethylphenyl)-cyclohexanol and 2-naphthylacetic acid/N,N'-carbonyldiimidazole. White crystals.

Melting point: 85°–87° C.

(25) trans-O-[2-(1,2,3,4-tetrahydro)naphthoyl]-4-(4-dimethylaminomethylphenyl)-cyclohexanol from trans-4-(4-dimethylaminomethylphenyl)-cyclohexanol and 2-(1,2,3,4-tetrahydro)naphthoic acid/N,N'-carbonyldiimidazole. White crystals.

Melting point: 95°–96° C.

(26) cis-O-[2-(1,2,3,4-tetrahydro) naphthoyl]-4-(4-dimethylaminomethylphenyl)-cyclohexanol from cis-4-(4-dimethylaminomethylphenyl)-cyclohexanol and 2-(1,2,3,4-tetrahydro) naphthoic acid/N,N'-carbonyldiimidazole. Colourless oil.

$^1$H-NMR spectrum (200 MHz, CDCl$_3$); signals at ppm: 1.55–1.85 (m,6H); 1.9–2.1 (m,3H); 2.15–2.32 (s+m,6+1H); 2.4–2.65 (m, 1H); 2.72–2.95 (m,3H); 3.05 (d,2H); 3.4 (s,2H); 5.1–5.2 (m, 1H); 7.05–7.3 (2m,8H).

(27) trans-O-(2-phenylpropionyl)-4-(4-dimethylaminomethylphenyl)-cyclohexanol from trans -4-(4-dimethylaminomethylphenyl)-cyclohexanol and 2-phenylpropionic acid/N,N'-carbonyldiimidazole. Colourless wax.

$^1$H-NMR spectrum (200 MHz, CDCl$_3$); signals at ppm: 1.25–1.7 (d+m,3+3H); 1.8–2.15 (m,5H); 2.3 (s,6H); 2.38–2.6 (m, 1H); 3.4 (s, 2H); 3.7 (q, 1H); 4.68–4.9 (m, 1H); 7.15 (d, 2H); 7.18–7.38 (d+m,2+5H).

(28) cis-O-(2-phenylpropionyl)-4-(4-dimethylaminomethylphenyl)-cyclohexanol from cis-4-(4-dimethylaminomethylphenyl)-cyclohexanol and 2-phenylpropionic acid/N,N'-carbonyldiimidazole. Colourless oil.

$^1$H-NMR spectrum (200 MHz, CDCl$_3$); signals at ppm: 1.3–1.7 (d+m,3+6H); 1.8–2.05 (m,2H); 2.25 (s,6H); 2.35–2.58 (m, 1H); 3.4 (s,2H); 3.78 (q, 1H); 5.0–5.1 (m, 1H); 7.0 (d,2H); 7.2 (d,2H); 7.25–7.4 (m,5H).

(29) trans-O-(4-fluorocinnamoyl)-4-(4-dimethylaminomethylphenyl)-cyclohexanol from trans-4-(4-dimethylaminomethylphenyl)-cyclohexanol and 4-fluorocinnamic acid/N,N'-carbonyldiimidazole. White crystals.

Melting point: 118°–120° C.

(30) cis-O-(4-fluorocinnamoyl)-4-(4-dimethylaminomethylphenyl)-cyclohexanol from cis-4-(4-dimethylaminomethylphenyl)-cyclohexanol and 4-fluorocinnamic acid/N,N'-carbonyldiimidazole. White crystals.

Melting point: 66°–68° C.

(31) trans-O-(4-chlorocinnamoyl)-4-(4-dimethylaminomethylphenyl)-cyclohexanol from trans-4-(4-dimethylaminomethylphenyl)-cyclohexanol and 4-chlorocinnamic acid/N,N'-carbonyldiimidazole. White crystals.

Melting point: 131°–133° C.

(32) cis-O-(4-chlorocinnamoyl)-4-(4-dimethylaminomethylphenyl)-cyclohexanol from cis-4-(4-dimethylaminomethylphenyl)-cyclohexanol and 1-chlorocinnamic acid/N,N'-carbonyldiimidazole. White crystals.

Melting point: 88°–90° C.

(33) trans-O-(4-[trifluoromethyl]-cinnamoyl)-4-(4-dimethylaminomethylphenyl)-cyclohexanol from trans-4-(4-dimethylaminomethylphenyl)-cyclohexanol and 4-(trifluoromethyl)-cinnamic acid/N,N'-carbonyldiimidazole. White crystals.

Melting point: 134°–136° C.

(34) cis-O-(4-[trifluoromethyl]-cinnamoyl)-4-(4-dimethylaminomethylphenyl)-cyclohexanol from cis-4-(4-dimethylaminomethylphenyl)-cyclohexanol and 4-(trifluoromethyl)-cinnamic acid/N,N'-carbonyldiimidazole. White crystals.

Melting point: 61°–63° C.

(35) trans-O-(5-chloro-2-thenoyl)-4-(4-dimethylaminomethylphenyl)-cyclohexanol from trans-4-(4-dimethylaminomethylphenyl)-cyclohexanol and 5-chloro-2-thiophenecarboxylic acid/N,N'-carbonyldiimidazole. White crystals.

Melting point: 95°–97° C.

(36) trans-O-nicotinoyl-4-(4-dimethylaminomethylphenyl)-cyclohexanol from trans-4-(4-dimethylaminomethylphenyl)-cyclohexanol and nicotinic acid/N,N'-carbonyldiimidazole. White crystals.

Melting point: 86°–88° C.

(37) trans-O-(2-furoyl)-4-(4-dimethylaminomethylphenyl)-cyclohexanol from trans-4-(4-dimethylaminomethylphenyl)-cyclohexanol and 2-furancarboxylic acid/N,N'-carbonyldiimidazole. White crystals.

Melting point: 58°–60° C.

(38) trans -O-(3,4-dimethoxyphenylacetyl)-4-(4-dimethylaminomethylphenyl)-cyclohexanol from trans-4-(4-dimethylaminomethylphenyl)-cyclohexanol and 3,4-dimethoxyphenylacetic acid/N,N'-carbonyldiimidazole. White crystals.

Melting point: 32°–34° C.

(39) trans-O-(4-amino-3-chlorophenylacetyl)-4-(4-dimethylaminomethylphenyl)-cyclohexanol from trans-4-(4-dimethylaminomethylphenyl)-cyclohexanol and 4-amino-3-chlorophenylacetic acid/N,N'-carbonyldiimidazole. White crystals.

Melting point: 83°–85° C.

(40) trans-O-(4-amino-3,5-dichlorophenylacetyl)-4-(4-dimethylaminomethylphenyl)-cyclohexanol from trans-4-(4-dimethylaminomethylphenyl)-cyclohexanol and 4-amino-3,5-dichlorophenylacetic acid/N,N'-carbonyldiimidazole. White crystals.

Melting point: 78°–80° C.

(41) trans-O-(4-chlorophenylacetyl)-4-(4-diethylaminomethylphenyl)-cyclohexanol from trans-4-(4-diethylaminomethylphenyl)-cyclohexanol and 4-chlorophenylacetic acid/N,N'-carbonyldiimidazole. Colourless oil.

$^1$H-NMR spectrum (200 MHz, CDCl$_3$); signals at ppm: 1.05 (t,6H); 1.4–1.72 (m,4H); 1.9–2.2 (m,4H); 2.4–2.6 (q+m,5H); 3.5 (s,2H); 3.6 (s,2H); 4.7–4.9 (m, 1H); 7.12 (d,2H); 7.18–7.35 (m,6H).

(42) trans-O-(4-chlorophenylacetyl)-4-(4-dipropylaminomethylphenyl)-cyclohexanol from trans-4-(4-dipropylaminomethylphenyl)-cyclohexanol and 4-chlorophenylacetic acid/N,N'-carbonyldiimidazole. Colourless oil.

$^1$H-NMR spectrum (200 MHz, CDCl$_3$); signals at ppm: 0.88 (t,6H); 1.38–1.7 (m,8H); 1.9–2.19 (m,4H); 2.35 (q,4H);

2.4–2.6 (m, 1H); 3.5 (s,2H); 3.6 (s,2H); 4.7–4.9 (m, 1H); 7.1 (d, 2H); 7.15–7.38 (m, 6H).

(43) trans-O-(4-chlorophenylacetyl)-4-(4-[N-methylbutylamino]methylphenyl)-cyclohexanol from trans-4-(4-[N-methylbutylamino]-methylphenyl)-cyclohexanol and 4-chlorophenylacetic acid/N,N'-carbonyldiimidazole. Colourless oil.

$^1$H-NMR spectrum (200 MHz, CDCl$_3$); signals at ppm: 0.9 (t, 3H); 1.2–1.7 (m, 8H); 1.8–2.15 (m, 4H); 2.18 (s, 3H); 2.35 (t,2H); 2.4–2.6 (m, 1H); 3.41 (s,2H); 3.6 (s,2H); 4.7–4.9 (m, 1H); 7.1 (d, 2H); 7.2–7.35 (m, 6H).

(44) trans-O-(4-chlorophenylacetyl)-4-(4-diallylaminomethylphenyl)-cyclohexanol from trans-4-(4-diallylaminomethylphenyl)-cyclohexanol and 4-chlorophenylacetic acid/N,N'-carbonyldiimidazole. Colourless oil.

$^1$H-NMR spectrum (200 MHz, CDCl$_3$); signals at ppm: 1.4–1.75 (m,4H); 1.9–2.2 (m,4H); 2.4–2.6 (m, 1H); 3.0–3.18 (dd,4H); 3.5 (s,2H); 3.6 (s,2H); 4.7–4.9 (m, 1H); 5.1–5.3 (m, 4H); 5.75–6.0 (m, 2H); 7.12 (d, 2H); 7.15–7.38 (m,6H).

(45) trans-O-(4-chlorophenylacetyl)-4-(4-[N-pyrrolidino]-methylphenyl)-cyclohexanol from trans-4-(4-[N-pyrrolidino]methylphenyl)-cyclohexanol and 4-chlorophenylacetic acid/N,N'-carbonyldiimidazole. White crystals.

Melting point: 57°–59° C.

(46) trans-O-(4-chlorophenylacetyl)-4-(4-[N-piperidino]-methylphenyl)-cyclohexanol from trans-4-(4-[N-piperidino]methylphenyl)-cyclohexanol and 4-chlorophenylacetic acid/N,N'-carbonyldiimidazole. White crystals.

Melting point: 87°–89° C.

(47) trans-O-(4-chlorophenylacetyl)-4-(4-[N-morpholino]-methylphenyl)-cyclohexanol from trans-4-(4-[N-morpholino]methylphenyl)-cyclohexanol and 4-chlorophenylacetic acid/N,N'-carbonyldiimidazole. White crystals.

Melting point: 114°–116° C.

(48) trans-O-(4-chlorophenylacetyl)-4-(4-[N-methyl -N'-piperazino]methylphenyl)-cyclohexanol from trans-4-(4-[N-methyl-N'-piperazino]methylphenyl)-cyclohexanol and 4-chlorophenylacetic acid/N,N'-carbonyldiimidazole. White crystals.

Melting point: 97°–99° C.

(49) trans-O-(3,4-[methylenedioxy]-phenylacetyl)-4-(4-dimethylaminomethylphenyl)-cyclohexanol from trans-4-(4-dimethylaminomethylphenyl)-cyclohexanol and 3,4-(methylenedioxy)-phenylacetic acid/N,N'-carbonyldiimidazole. Colourless oil.

$^1$H-NMR spectrum (200 MHz, CDCl$_3$); signals at ppm: 1.4–1.7 (m, 4H), 1.8–2.0 (m, 2H), 2.0–2.15 (m,2H), 2.25 (s,6H), 2.4–2.6 (m, 1H), 3.38 (s,2H), 3.5 (s,2H), 4.7–4.9 (m, 1H), 5.94 (s,2H), 6.7–6.85 (m,3H), 7.1–7.3 (m,4H).

EXAMPLE 3 cis-O-(4-Chlorobenzoyl)-4-(4-dimethylaminomethylphenyl)-cyclohexanol 0.24 g (0.001 mol) of cis-4-(4-dimethylaminomethylphenyl)-cyclohexanol, 0.34 ml (0.0025 mol) of triethylamine and 0.12 g (0.001 mol) of dimethylaminopyridine are dissolved in 20 ml of methylene chloride, mixed with 0.175 g (0.001 mol) of 4-chlorobenzoylchloride and stirred for 12 hours at ambient temperature. The reaction mixture is combined with water and adjusted to pH 12–13 using sodium hydroxide solution.

The methylene chloride phase is separated off, the aqueous phase is extracted several times with methylene chloride and the combined organic phases are washed with saturated saline solution, dried and evaporated down in vacuo. The residue is purified by column chromatography (aluminium oxide neutral, activity stage III, ICN; petroleum ether/ethyl acetate=45:1) White crystals.

Melting point: 96°–97° C. Yield: 0.27 g (73% of theory)
$^1$H-NMR spectrum (200 MHz, CDCl$_3$); signals at ppm: 1.7–2.0 (m,6H); 2.1–2.25 (m,2H); 2.28 (s,6H); 2.55–2.75 (m, 1H); 3.4 (s,2H); 5.33–5.4 (m, 1H); 7.15–7.3 (m,4H); 7.45 (d, 2H); 8.2 (d, 2H).

EXAMPLE 4 trans-O-Acetyl-4-(4-diethylaminomethylphenyl)-cyclohexanol

A solution of 1 g (3.75 mmol) of trans-O-acetyl-4-(4-chloromethylphenyl)-cyclohexanol in 10 ml of dimethylformamide is mixed with 0.52 g (3.75 mmol) of potassium carbonate and 0.27 g (3.75 mmol) of diethylamine. This mixture is heated to 50° C. for 6 hours with stirring, then water is added and the mixture is extracted with methylene chloride. The organic phase is dried, evaporated down in vacuo and the residue remaining is purified by column chromatography (aluminium oxide basic, activity stage III, ICN; petroleum ether/ethyl acetate=15:1). Colourless oil.

Yield: 0.79 g (69% of theory) $^1$H-NMR spectrum (200 MHz, CDCl$_3$); signals at ppm: 1.05 (t,6H); 1.45–1.75 (m,4H); 1.9–2.2 (s+m,7H); 2.4–2.6 (q+m,5H); 3.55 (s,2H); 4.68–4.9 (m, 1H); 7.12 (d,2H); 7.28 (d, 2H).

The following substances were synthesised analogously:

(1) trans-O-acetyl-4-(4-dipropylaminomethylphenyl)-cyclohexanol from trans-O-acetyl-4-(4-chloromethylphenyl)-cyclohexanol and dipropylamine. Colourless oil.

$^1$H-NMR spectrum (200 MHz, CDCl$_3$); signals at ppm: 0.9 (t,6H); 1.35–1.75 (m,8H); 1.9–2.2 (s+m,7H); 2.3–2.6 (q+m, 5H); 3.5 (s, 2H); 4.65–4.9 (m, 1H); 7.1 (d, 2H); 7.25 (d, 2H).

(2) trans-O-acetyl-4-(4-[N-methylbutylamino]-methylphenyl)-cyclohexanol from trans-O-acetyl-4-(4-chloromethylphenyl)-cyclohexanol and N-methylbutylamine. Colourless oil.

$^1$H-NMR spectrum (200 MHz, CDCl$_3$); signals at ppm: 0.9 (t,3H); 1.2–1.75 (m,10H); 1.9–2.2 (2s+m,8H); 2.38 (t,2H); 2.4–2.6 (m, 1H); 3.45 (s,2H); 4.7–4.9 (m, 1H); 7.15 (d,2H); 7.25 (d,2H).

(3) trans-O-acetyl-4-(4-diallylaminomethylphenyl)-cyclohexanol from trans-O-acetyl-4-(4-chloromethylphenyl)-cyclohexanol and diallylamine. Colourless oil.

$^1$H-NMR spectrum (200 MHz, CDCl$_3$); signals at ppm: 1.4–1.7 (m,4H); 1.9–2.18 (s+m,7H); 2.4–2.6 (m, 1H); 3.09 (dd,4H); 3.52 (s,2H); 4.7–4.9 (m, 1H); 5.01–5.3 (m,4H); 5.75–6.0 (m,2H); 7.12 (d,2H); 7.35 (d,2H).

(4) trans-O-acetyl-4-(4-[N-pyrrolidino]methylphenyl)-cyclohexanol from trans-O-acetyl-4-(4-chloromethylphenyl)-cyclohexanol and pyrrolidine. Colourless crystals.

Melting point: 43°–45° C.

(5) trans-O-acetyl-4-(4-[N-morpholino]methylphenyl)-cyclohexanol from trans-O-acetyl-4-(4-chloromethylphenyl)-cyclohexanol and morpholine. Colourless crystals.

Melting point: 53°–55° C.
(6) trans-O-acetyl-4-(4-[N-piperidino]methylphenyl)-cyclohexanol from trans-O-acetyl-4-(4-chloromethylphenyl)-cyclohexanol and piperidine. Colourless crystals.
Melting point: 62°–64° C.

(7) trans-O-acetyl-4-[N-methyl-N'-piperazino]methylphenyl)-cyclohexanol from trans-O-acetyl-4-(4-chloromethylphenyl)-cyclohexanol and N-methylpiperazine. Colourless crystals.
Melting point: 50°–52° C.

EXAMPLE 5 trans-O-(4-Chlorophenylacetyl)-4-(4-methylaminomethylphenyl)-cyclohexanol

A solution of 8.9 g (0.019 Mol) of trans-O-(4-chlorophenylacetyl)-4-(4-N-[tert.-butoxycarbonyl]-methylaminomethyl)phenyl-cyclohexanol in 200 ml of methylene chloride is combined with 35 ml of trifluoroacetic acid and stirred for 2 hours at ambient temperature. Then the volatile components are distilled off in vacuo, the residue is taken up in methylene chloride and washed to neutral with saturated sodium hydrogen carbonate solution. The organic phase is dried over sodium sulphate and evaporated down in vacuo. A yellowish oil remains which is purified by column chromatography (aluminium oxide basic, activity stage III, ICN; petroleum ether/ethyl acetate/methanol=10:10:1). Yellowish white crystals are obtained, melting point 65°–67° C.

Yield: 6.4 g (91% of theory). $^1$H-NMR spectrum (200 MHz, CDCl$_3$); signals at ppm: 1.4–1.7 (m,4H); 1.8–2.0 (m,2H), 2.0–2.2 (m,2H), 2.4–2.6 (s+m,3+1H), 3.58 (s,2H), 3.7 (s,2H); 4.7–4.9 (m, 1H), 7.1–7.35 (m, 8H).

The following substance was synthesised analogously:
(1) O-(4-chlorophenylacetyl)-4-(4-methylaminomethylphenyl)-cyclohexanol (cis/trans mixture)

from O-(4-chlorophenylacetyl)-4-(4-N-[tert.-butoxycarbonyl]-methylaminomethyl)phenyl-cyclohexanol (cis/trans mixture) and trifluoroacetic acid. Yellow oil.

R$_f$ value (aluminium oxide; petroleum ether/ethyl acetate/methanol=10:10:1): 0.28–0.53.

EXAMPLE 6

O-(4-Chlorophenylacetyl)-4-(4-N-[carboxamidomethyl]-methylaminomethyl)phenyl-cyclohexanol (cis/trans mixture)

A mixture of 1.0 g (0.0027 mol) of O-(4-chlorophenylacetyl)-4-(4-methylaminomethylphenyl)-cyclohexanol (cis/trans mixture) (0.5 g (0.0027 mol) of iodoacetamide, 0.37 g (0.0027 mol) of potassium carbonate and 5 ml of dimethylformamide is heated to 50° C. for 2 hours with stirring. After it has cooled to ambient temperature, water is added and the mixture is extracted with ethyl acetate. The organic phase is dried over sodium sulphate, the volatile components are distilled off in vacuo and the residue is purified by column chromatography (aluminium oxide basic, activity stage III, ICN; petroleum ether/ethyl acetate/methanol=60:40:2.5).

A white crystalline product is obtained which sinters from 110° C. and melts between 128°–132° C.

$^1$H-NMR spectrum (200 MHz, CDCl$_3$); signals at ppm: 1.4–1.75 (m,5H); 1.8–2.2 (m,3H), 2.32 (dd,3H), 2.4–2.63 (m, 1H), 3.0 (dd, 2H), 3.5–3.7 (dd+dd, 2+2H), 4.7–4.9 (m, 0.5H), 5.08–5.15 (m,0.5H), 7.0–7.4 (m,8H).

The following substances were synthesised analogously:
(1) trans-O-(4-chlorophenylacetyl)-4-(4-N-[carbethoxymethyl]-methylaminomethyl)phenyl-cyclohexanol from trans-O-(4-chlorophenylacetyl)-4-(4-methylaminomethylphenyl)-cyclohexanol, ethylbromoacetate and potassium carbonate/dimethylformamide. White solid product.
Melting point: 40°–42° C.

(2) trans-O-(4-chlorophenylacetyl)-4-(4-N-[3-hydroxypropyl]-methylaminomethyl)phenyl-cyclohexanol from trans-O-(4-(chlorophenylacetyl)-4-(4-methylaminomethylphenyl)-cyclohexanol, 3-bromopropanol and potassium carbonate/dimethylformamide. White crystals.
Melting point: 75°–77° C.

EXAMPLE 7 trans-O-(4-Chlorophenylacetyl)-4-(4-dimethylaminomethylphenyl)-cyclohexanol-hydrochloride A solution of 0.39 g (0.001 mol) of trans-O-(4-chlorophenylacetyl)-4-(4-dimethylaminomethylphenyl)-cyclohexanol in 10 ml of diethyl ether is combined at ambient temperature, with stirring, with a 1.5 times equimolar amount of hydrogen chloride in isopropanol added dropwise. The precipitate formed is left for 1 hour at ambient temperature, suction filtered, washed repeatedly with diethyl ether and dried. White crystals are obtained, melting point 231°–233° C.

Yield: 0.32 g (76% of theory).

| $C_{23}H_{29}Cl_2NO_2$ (422.40) | | | |
|---|---|---|---|
| Calculated: | C 65.40 | H 6.92 | N 3.32 | Cl 16.79 |
| Found: | 65.33 | 7.06 | 3.45 | 16.92 |

EXAMPLE 8 trans-O-(4-Chlorophenylacetyl)-4-(4-dimethylaminomethylphenyl)-cyclohexanol-tartrate First 0.15 g (0.001 mol) of anhydrous tartaric acid and then 0.39 g (0.001 mol) of trans-O-(4-chlorophenylacetyl)-4-(4-dimethylaminomethylphenyl)-cyclohexanol are dissolved in 7 ml of absolute ethanol. Diethyl ether is then added to the clear solution until it becomes slightly cloudy and it is then left to stand for 8 hours at +4° C. The crystalline product precipitated is suction filtered, washed with diethyl ether and dried.

| Melting point: 169–171° C. | | | |
|---|---|---|---|
| Yield: 0.46 g (86% of theory). | | | |
| $C_{27}H_{34}ClNO_8$ (536.02) | | | |
| Calculated: | C 60.50 | H 6.39 | N 2.61 | Cl 6.61 |
| Found: | 60.37 | 6.38 | 2.65 | 6.73 |

The following Examples illustrate the preparation of some pharmaceutical administration forms:

EXAMPLE I

Tablets containing 5 mg of trans-O-(4-chlorophenylacetyl)-4-(4-dimethylaminomethyl-phenyl)-cyclohexanol

| Composition: | |
|---|---|
| 1 tablet contains: | |
| Active substance | 5.0 mg |
| Lactose | 148.0 mg |
| Potato starch | 65.0 mg |
| Magnesium stearate | 2.0 mg |
| | 220.0 mg |

Method of Preparation

A 10% mucilage is prepared from potato starch by heating. The active substance, lactose and the remaining potato starch are mixed together and granulated with the above mucilage through a 1.5 mm mesh screen. The granules are dried at 45° C., rubbed through the same screen again, mixed with magnesium stearate and compressed to form tablets.

Weight of tablet: 220 mg Punch: 9 mm

EXAMPLE II

Coated tablets containing 5 mg of trans-O-(4-chlorophenylacetyl)-4-(4-dimethylaminomethyl-phenyl)-cyclohexanol The tablets prepared according to Example I are coated, by a known method, with a coating consisting essentially of sugar and talc. The finished coated tablets are polished with beeswax.

Weight of coated tablet: 300 mg

EXAMPLE III

Suppositories containing 5 mg of trans-O-(4-chlorophenylacetyl)-4-(4-dimethylaminomethyl-phenyl)-cyclohexanol

| Composition: | |
|---|---|
| 1 suppository contains: | |
| Active substance | 5.0 mg |
| Suppository mass (e.g. Witepsol W 45 ®) | 1695.0 mg |
| | 1700.0 mg |

Method of Preparation

The finely powdered active substance is suspended in the molten suppository mass which has been cooled to 40° C. At 37° C. the mass is poured into slightly chilled suppository moulds.

Weight of suppository 1.7 g

EXAMPLE IV

Capsules containing 5 mg of trans-O-(4-[trifluoromethyl]-phenylacetyl)-4-(4-dimethylaminomethyl-phenyl)-cyclohexanol

| Composition: | |
|---|---|
| 1 capsule contains: | |
| Active substance | 5.0 mg |
| Lactose | 82.0 mg |
| Starch | 82.0 mg |
| Magnesium stearate | 1.0 mg |
| | 170.0 mg |

Method of Preparation:

The powder mixture is mixed thoroughly and packed into size 3 hard gelatine capsules in a capsule filling machine, the end weight being continuously monitored.

EXAMPLE V

Tablets containing 5 mg of trans-O-(4-bromophenylacetyl)-4-(4-dimethylaminomethyl-phenyl)-cyclohexanol

| Composition: | |
|---|---|
| 1 tablet contains: | |
| Active substance | 5.0 mg |
| Lactose | 148.0 mg |
| Potato starch | 65.0 mg |
| Magnesium stearate | 2.0 mg |
| | 220.0 mg |

Method of Preparation:

A 10% mucilage is prepared from potato starch by heating. The active substance, lactose and the remaining potato starch are mixed together and granulated with the above mucilage through a 1.5 mm mesh screen. The granules are dried at 45° C., rubbed through the same screen again, mixed with magnesium stearate and compressed to form tablets.

Weight of tablet: 220 mg Punch: 9 mm

EXAMPLE VI

Cream for topical administration containing 1 g of trans-O-(4-chlorophenylacetyl)-4-(4-dimethylaminomethyl-phenyl)-cyclohexanol A formulation for topical administration of the compounds of formula I may have the following composition:

| | | |
|---|---|---|
| 1. | Active substance | 1.0 g |
| 2. | Stearyl alcohol | 4.0 g |
| 3. | Cetyl alcohol | 4.0 g |
| 4. | Mineral oil | 3.0 g |
| 5. | Polysorbate 60 | 4.5 g |
| 6. | Sorbitan stearate | 4.5 g |
| 7. | Propyleneglycol | 10.0 g |
| 8. | Methylparaben | 0.18 g |
| 9. | Propylparaben | 0.02 g |
| 10. | Water q.s. ad | 100.00 g |

Ingredients 2–6 are heated to 80° C. until they have all melted. Then ingredient 1 is dissolved in the oily phase. Ingredients 7 and 10 are heated to 90° C. and ingredients 8 and 9 are dissolved in the aqueous phase thus obtained. The aqueous phase is then added to the oil phase and quickly stirred to obtain an emulsion. The mixture is then slowly cooled to 50° C. in order to solidify the emulsion. The preparation is cooled to ambient temperature whilst stirring is continued.

The following Example describes the preparation of a feed for laying hens:

EXAMPLE VII

Feed for laying hens containing as active substance trans-O-(4-chlorophenylacetyl)-4-(4-dimethylaminomethylphenyl)-cyclohexanol

| Maize | 633 g/kg |
|---|---|
| Soya bean flour | 260 g/kg |
| Meatmeal | 40 g/kg |
| Edible fat | 25 g/kg |
| Soya oil | 17 g/kg |
| Bicalcium phosphate | 12 g/kg |
| Calcium carbonate | 6 g/kg |
| Vitamin/mineral mixture | 5 g/kg |
| Active substance | 2 g/kg |

These components in the quantities specified, when mixed thoroughly, yield 1 kg of feed.

We claim:

1. A compound of the formula Ia

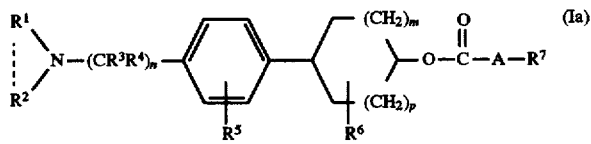

wherein n, m and p each denote the number 1, $R^1$ denotes a hydrogen atom, a straight-chained or branched $C_{1-4}$-alkyl group which may be substituted by an aminocarbonyl group or, in the 2-, 3- or 4-position, by a hydroxy or alkoxy group, or a 2-propenylene group, $R^2$ denotes a hydrogen atom or a $C_{1-4}$-alkyl group, $R^3$ to $R^6$ each denote a hydrogen atom, $R^7$ denotes a phenyl group optionally substituted in the 4-position by a fluorine, chlorine or bromine atom or by a methyl, trifluoromethyl, methoxy, phenyl or nitro group, a 3,4-dichlorophenyl, 2,4-dichlorophenyl, 4-chloro-3-methylphenyl, 4-amino-3-chlorophenyl, 3,4-dimethoxyphenyl, 3,4-methylenedioxyphenyl, 4-amino-3,5-dichlorophenyl or 2-naphthyl group, and A denotes a bond, a straight-chained or branched $C_{1-5}$-alkylene group or a $C_{2-3}$-alkenylene group, wherein all the above-mentioned alkyl and alkoxy moieties, unless otherwise specified, may contain 1 to 3 carbon atoms, or an enantiomer, diastereomer, geometric isomer or pharmaceutically acceptable salt thereof.

2. A compound selected from the group consisting of:
(a) cis-O-(4-chlorobenzoyl)-4-(4-dimethylaminomethylphenyl)-cyclohexanol;
(b) cis-O-(4-phenyl-3-butenoyl)-4-(4-dimethylaminomethylphenyl)-cyclohexanol;
(c) trans-O-(4-chlorophenylacetyl)-4-(4-dimethylaminomethylphenyl)-cyclohexanol;
(d) cis-O-(5-methylhexanoyl)-4-(4-dimethylaminomethylphenyl)-cyclohexanol;
(e) trans-O-(2-phenylpropionyl)-4-(4-dimethylaminomethylphenyl)-cyclohexanol;
(f) trans-O-(4-fluorophenylacetyl)-4-(4-dimethylaminomethylphenyl)-cyclohexanol;
(g) trans-O-(3,4-dichlorophenylacetyl)-4-(4-dimethylamino-methylphenyl)-cyclohexanol;
(h) cis-O-(4-fluorocinnamoyl)-4-(4-dimethylaminomethylphenyl)-cyclohexanol;
(i) trans-O-(p-tolylacetyl)-4-(4-dimethylaminomethylphenyl)-cyclohexanol;
(j) trans-O-(4-[trifluoromethyl]-phenylacetyl)-4-(4-dimethylaminomethylphenyl)-cyclohexanol;
(k) trans-O-(2-naphthylacetyl)-4-(4-dimethylaminomethyl-phenyl)-cyclohexanol;
(l) trans-O-(4-nitrophenylacetyl)-4-(4-dimethylaminomethylphenyl)-cyclohexanol;
(m) trans-O-(4-bromophenylacetyl)-4-(4-dimethylaminomethylphenyl)-cyclohexanol;
(n) trans-O-(2,4-dichlorophenylacetyl)-4-(4-dimethylaminomethylphenyl)-cyclohexanol;
(o) trans-O-([4-amino-3-chlorophenyl]acetyl)-4-(4-dimethylaminomethylphenyl)-cyclohexanol;
(p) trans-O-(4-methoxyphenylacetyl)-4-(4-dimethylamino-methylphenyl)-cyclohexanol;
(q) trans-O-(4-chlorophenylacetyl)-4-(4-methylaminomethylphenyl)-cyclohexanol; (r) trans-O-phenylacetyl-4-(4-dimethyl-aminomethylphenyl)-cyclohexanol;

or a pharmaceutically acceptable salt thereof.

3. A pharmaceutical composition comprising a compound in accordance with claims 1 or 2 together with one or more inert carriers and/or diluents.

4. A method for inhibiting cholesterol biosynthesis in an animal suffering from over production of cholesterol, which method comprises administering to said animal an amount of a compound in accordance with claims 1 or 2 which is sufficient to inhibit cholesterol biosynthesis.

5. A method for treating hyperlipidaemia in an animal suffering from over production of cholesterol, which method comprises administering to said animal an amount of a compound in accordance with claims 1 or 2 which is sufficient to inhibit cholesterol biosynthesis.

6. Trans-O-(p-tolylacetyl)-4-(4-dimethylaminomethylphenyl)-cyclohexanol, or a pharmaceutically acceptable salt thereof.

7. Trans-O-phenylacetyl-4-(4-dimethylaminomethylphenyl)-cyclohexanol, or a pharmaceutically acceptable salt thereof.

* * * * *